United States Patent
Benedini et al.

(10) Patent No.: US 9,012,435 B2
(45) Date of Patent: *Apr. 21, 2015

(54) GLUCOCORTICOIDS ATTACHED TO NITRATE ESTERS VIA AN AROMATIC LINKER IN POSITION 21 AND THEIR USE IN OPHTHALMOLOGY

(71) Applicant: Nicox S.A., Sophia Antipolis—Valbonne (FR)

(72) Inventors: Francesca Benedini, San Donato Milanese (IT); Annalisa Bonfanti, Besana Brianza (IT); Valerio Chiroli, Milan (IT); Rebecca Steele, Solaro (IT); Ennio Ongini, Segrate (IT); Stefano Biondi, Pero (IT)

(73) Assignee: Nicox S.A., Valbonne (FR)

( * ) Notice: Subject to any disclaimer, the term of this patent is extended or adjusted under 35 U.S.C. 154(b) by 0 days.

This patent is subject to a terminal disclaimer.

(21) Appl. No.: 13/946,794

(22) Filed: Jul. 19, 2013

(65) Prior Publication Data

US 2013/0303499 A1 Nov. 14, 2013

Related U.S. Application Data

(62) Division of application No. 13/056,921, filed as application No. PCT/EP2009/058572 on Jul. 7, 2009, now Pat. No. 8,518,920.

(60) Provisional application No. 61/122,896, filed on Dec. 16, 2008, provisional application No. 61/085,294, filed on Jul. 31, 2008.

(51) Int. Cl.
*A61K 31/58* (2006.01)
*C07J 71/00* (2006.01)
*C07J 41/00* (2006.01)

(52) U.S. Cl.
CPC ............ *C07J 71/0031* (2013.01); *C07J 41/005* (2013.01)

(58) Field of Classification Search
CPC .............................. C07J 71/0031; A61K 31/58
USPC ........................................................ 514/174
See application file for complete search history.

(56) References Cited

FOREIGN PATENT DOCUMENTS

| WO | WO 03/064443 A2 | 8/2003 |
| WO | WO 2007/025632 A2 | 3/2007 |

OTHER PUBLICATIONS

F. Galassi et al., "A Topical Nitric Oxide-Releasing Dexamethasone Derivative: effects on intraocular Pressure and Ocular Haemodynamics in a Rabbit Glaucoma Model", British Journal of Ophthalmology, Nov. 2006, pp. 1414-1419, vol. 90, No. 11.

*Primary Examiner* — Barbara P Badio
(74) *Attorney, Agent, or Firm* — Arent Fox LLP

(57) ABSTRACT

The invention relates to nitrooxy derivatives of fluocinolone acetonide, triamcinolone acetonide, betamethasone and beclomethasone, methods for their preparation, pharmaceutical compositions containing these compounds, and methods of using these compounds and compositions for treating diabetic macular edema, diabetic retinopathy, macular degeneration, age-related macular degeneration and other diseases of retina and macula lutea.

3 Claims, 4 Drawing Sheets

Figure 1A:
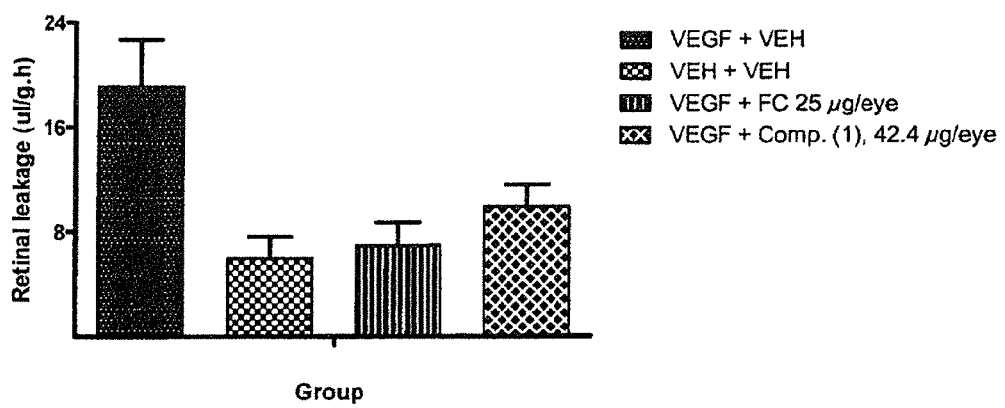

GLUCOCORTICOIDS ATTACHED TO NITRATE ESTERS VIA AN AROMATIC LINKER IN POSITION 21 AND THEIR USE IN OPHTHALMOLOGY

CROSS-REFERENCE TO RELATED APPLICATION

This application is a Divisional of U.S. Pat. No. 8,518,920, which is a National Stage entry of International Application No. PCT/EP2009/058572, filed Jul. 7, 2009, which claims the benefit of U.S. Provisional Patent Application No. 61/122,896 filed Dec. 16, 2008, and U.S. Provisional Patent Application No. 61/085,294 filed Jul. 31, 2008, the disclosure of the prior applications is hereby incorporated in its entirety by reference herein.

The invention relates to nitrooxy derivatives of steroids, methods for their preparation, pharmaceutical compositions containing these compounds, and methods of using these compounds and compositions for treating ocular diseases, in particular diabetic macular edema, diabetic retinopathy, macular degeneration, age-related macular degeneration and other diseases of retina and macula lutea.

The retina is the part of the eye that is sensitive to light. The macula lutea is the region of the retina that allows us to read and recognize faces. Diseases of the macula, such as age-related macular degeneration and diabetic macular edema, account for major causes of blindness.

To combat these diseases, a variety of drugs have been investigated for their effects on blinding disorders.

Currently, these drugs are delivered to the macula and retina via surgical procedures such as intravitreal or periorbital injections, or via systemic routes. Surgical methods often require repeated injections and may lead to serious ocular complications, including endophthalmitis, retinal detachment, and vitreous hemorrhage. Likewise, systemic administration is associated with a variety of potential systemic side effects and with the difficulty of delivering therapeutic levels of the drugs to the retina.

Recently, there have been many reports of the effectiveness of intravitreal triamcinolone acetonide for the treatment of diffuse macular edema, refractory to laser treatment.

Intravitreal triamcinolone injections are however associated with many ocular complications. The complications of intravitreal triamcinolone therapy include steroid induced elevation of intraocular pressure, cataractogenesis, post-operative infectious and non-infectious endophthalmitis, and pseudo-endophthalmitis.

At present chemotherapy, steroids and carbonic anhydrase inhibitors as major efficacy are used in symptomatic therapy, but their effectiveness is not established and their administration for a long time leads to occurrence of side effects such as cataract, steroid induced elevation of intraocular pressure, glaucoma, and infections thus continuous use of these drugs in chronic diseases, such as diabetes mellitus, is difficult under the circumstances.

EP 0929565 discloses compounds of general formula B—$X_1$—$NO_2$ wherein B contains a steroid residue, in particular hydrocortisone, and $X_1$ is a bivalent connecting bridge which is a benzyl ring, an alkyl chain or a ether. The compounds may be used in the treatment of ocular disorders.

EP 1 475 386 discloses compounds of formula A-B—C—$NO_2$ wherein A contains a steroid residue and B—C is a bivalent connecting bridge which contains an antioxidant residue. The compounds may be used in the treatment of oxidative stress and/or endothelial dysfunctions.

In the disclosed compounds the antioxidant linker is linked to the 21-OH of the steroid through a carboxylic group forming an ester bond.

WO 03/64443 discloses compounds of general formula B—$X_1$—$NO_2$ wherein B contains a steroid residue and $X_1$ is a bivalent connecting bridge which is a benzyl ring or a heterocyclic linker. The compounds may be used in the treatment of ocular diseases WO 07/025,632 discloses compounds of formula R—Z—X—$ONO_2$ wherein R—X contains triamcinolone acetonide, betamethasone valerate or prednisolone ethylcarbonate residue and $X_1$ is a bivalent connecting bridge which is an aromatic ring, an alkyl chain, an ether, ferulic acid, vanillic acid or an heterocyclic ring. The compounds may be used in the treatment of skin or mucosal membrane diseases and in particular in the treatment of atopic dermatitis, contact dermatitis and psoriasis.

F. Galassi et al. Br J Ophthalmology 2006, 90, 1414-1419 discloses the effects of an dexamethasone 21-[(4-nitrooxymethyl)]benzoate in a model of experimental corticosteroid-induced glaucoma in the rabbit. The NO-releasing dexamethasone was administered topically twice a day, the results show that the compound may prevent the intraocular pressure increase, the impairment of retro bulbar circulation, and the morphological changes in the ciliary bodies possibly induced by topical treatment with corticosteroids.

It is, an object of the present invention to provide nitrooxy-derivatives of steroids for treating inflammatory diseases.

Another object of the present invention to provide nitrooxy-derivatives of steroids for the prevention or the treatment of ocular diseases, in particular diabetic macular degeneration, diabetic retinopathy, age-related macular degeneration and other diseases of retina and macula lutea. In one aspect of the invention, one or more of these compounds reduce the side effects associated with the standard therapy with steroids. In a further embodiment, one or more of these compounds possess improved pharmacological activity compared to current standard therapy.

An object of the present invention is a compound of formula (I) or a salt or a stereoisomer thereof

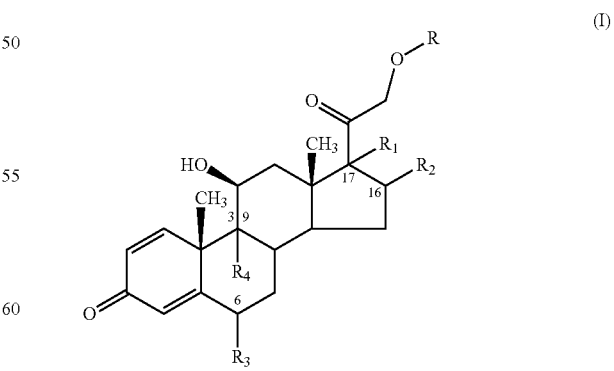

wherein
$R_1$ is OH, $R_2$ is $CH_3$, or $R_1$ and $R_2$ taken together are the group of formula (II)

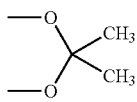
(II)

$R_3$ is a hydrogen atom or F and $R_4$ is F or Cl, with the proviso that:
  when $F_1$ is OH and $R_2$ is $CH_3$, $R_3$ is a hydrogen atom;
  when $F_1$ and $R_2$ taken together are the group of formula (II), $R_4$ is F;
$R_1$, $R_2$, $R_3$ and $R_4$ are linked to the carbon atoms in 17, 16, 6 and 9 of the steroidal structure in position α or β;
R is:

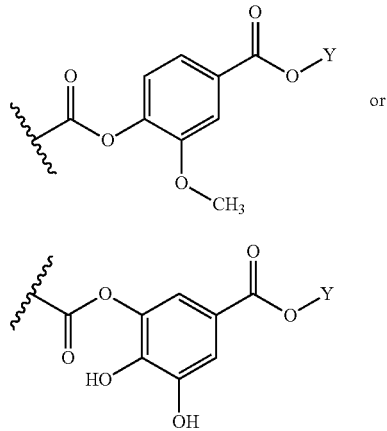

(III)

or (IV)

wherein
Y is selected from:
1) —$R_5$—CH(ONO$_2$)$R_6$
2) —$R_5$—CH(ONO$_2$)—(CR$_7$R$_8$)$_n$—CH(ONO$_2$)$R_9$
3) —[(CH$_2$)$_o$—X]$_p$—(CH$_2$)$_q$—CH(ONO$_2$)$R_9$
4) —[(CH$_2$)$_o$—(X)]$_p$—(CH$_2$)$_q$—CH(ONO$_2$)—(CR$_7$R$_8$)$_n$—CH(ONO$_2$)$R_9$
wherein
$R_5$ is a straight or branched $C_1$-$C_{10}$ alkylene; preferably $R_5$ is a straight $C_1$-$C_6$ alkylene;
$R_6$ is H or a straight or branched $C_1$-$C_6$ alkyl, preferably $R_6$ is H or —CH$_3$;
$R_7$ and $R_8$ at each occurrence are independently H or a straight or branched $C_1$-$C_6$ alkyl; preferably $R_7$ and $R_8$ at each occurrence are independently H or CH$_3$;
$R_9$ is H or a straight or branched $C_1$-$C_6$ alkyl, preferably $R_9$ is H or —CH$_3$;
n is an integer from 0 to 6; preferably n is 0 or 1;
o is an integer from 1 to 6; preferably o is an integer from 2 to 4, more preferably o is 2;
p is an integer from 1 to 6; preferably p is an integer from 1 to 4; more preferably p is 1 or 2;
q is an integer from 0 to 6; preferably q is from 0 to 4, more preferably is 0 or 1;
X is O, S or NR$_{10}$ wherein $R_{10}$ is H or a $C_1$-$C_4$ alkyl; preferably X is O;
with then proviso that the invention does not include the compounds of formula (I) wherein $R_1$ and $R_2$ taken together are the group of formula (II)

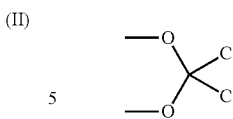
(II)

$R_4$ is F and $R_3$ is a hydrogen atom, and R is the compound of formula (III) wherein and Y is —$R_5$—CH(ONO$_2$)$R_6$ and $R_6$ is H.

In another embodiment of the invention, there is provided a compound of formula (I)

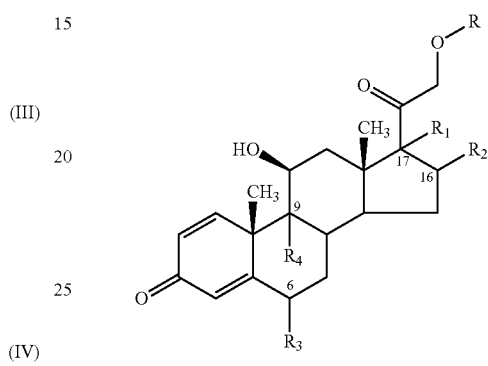

wherein
$R_4$ is F, $R_3$ is F, and
$R_1$ and $R_2$ taken together are the group of formula (II)

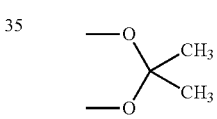
(II)

$R_1$, $R_2$, $R_3$ and $R_4$ are linked to the carbon atoms in 17, 16, 6 and 9 of the steroidal structure in position α;
R is:

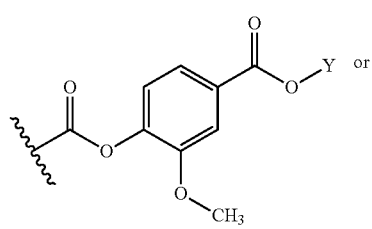
(III)

or

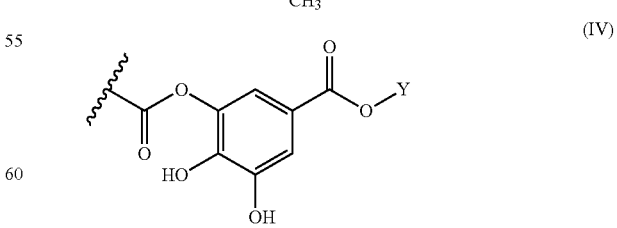
(IV)

wherein
Y is selected from:
1) —$R_5$—CH(ONO$_2$)$R_6$
2) —$R_b$—CH(ONO$_2$)—(CR$_7$R$_8$)$_n$—CH(ONO$_2$)$R_9$ 3) —[(CH$_2$)$_o$—X]$_p$—(CH$_2$)$_q$—CH(ONO$_2$)R$_9$
4) —[(CH$_2$)$_o$—(X)]$_p$—(CH$_2$)$_q$—CH(ONO$_2$)—(CR$_7$R$_8$)$_n$—CH(ONO$_2$)R$_9$ wherein R$_5$ is a straight or branched C$_1$-C$_{10}$ alkylene; preferably R$_5$ is a straight C$_1$-C$_6$ alkylene;

R$_6$ is H or a straight or branched C$_1$-C$_6$ alkyl, preferably R$_6$ is H or —CH$_3$;

R$_7$ and R$_8$ at each occurrence are independently H or a straight or branched C$_1$-C$_6$ alkyl; preferably R$_7$ and R$_8$ at each occurrence are independently H or CH$_3$;

R$_9$ is H or a straight or branched C$_1$-C$_6$ alkyl, preferably R$_9$ is H or —CH$_3$;

n is an integer from 0 to 6; preferably n is 0 or 1;

o is an integer from 1 to 6; preferably o is an integer from 2 to 4, more preferably o is 1;

p is an integer from 1 to 6; preferably p is an integer from 1 to 4; more preferably p is 1 or 2;

q is an integer from 0 to 6; preferably q is from 0 to 4, more preferably is 0 or 1;

X is O, S or NR$_{10}$ wherein R$_{10}$ is H or a C$_1$-C$_4$ alkyl; preferably X is O.

In another aspect of the invention, there is provided a compound of formula (I)

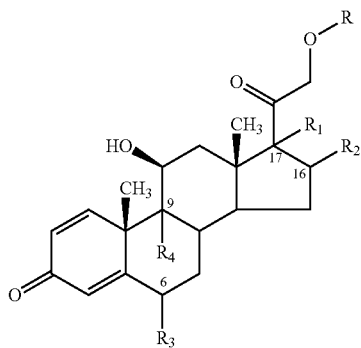

wherein

R$_1$ and R$_2$ taken together are the group of formula (II)

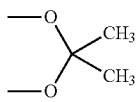
(II)

R$_4$ is F and R$_3$ is a hydrogen atom;

R$_2$ and R$_4$ are linked to the carbon atoms in 17, 16 and 9 of the steroidal structure in position α;

R is:

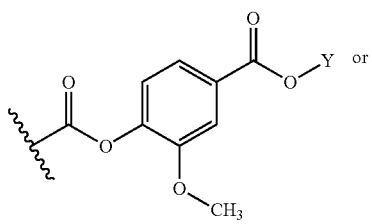
(III)

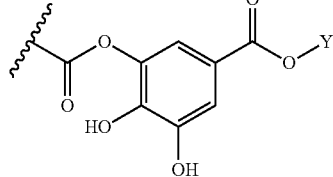
(IV)

wherein

Y is selected from:

1) —R$_5$—CH(ONO$_2$)R$_6$
2) —R$_5$—CH(ONO$_2$)—(CR$_7$R$_8$)$_n$—CH(ONO$_2$)R$_9$
3) —[(CH$_2$)$_o$—X]$_p$—(CH$_2$)$_q$—CH(ONO$_2$)R$_9$
4) [(CH$_2$)$_o$—(X)]$_p$—(CH$_2$)$_q$—CH(ONO$_2$)—(CR$_7$R$_8$)$_n$—CH(ONO$_2$)R$_9$ wherein R$_5$ is a straight or branched C$_1$-C$_{10}$ alkylene; preferably R$_5$ is a straight C$_1$-C$_6$ alkylene;

R$_6$ is a straight or branched C$_1$-C$_6$ alkyl, preferably R$_6$ is —CH$_3$;

R$_7$ and R$_8$ at each occurrence are independently H or a straight or branched C$_1$-C$_6$ alkyl; preferably R$_7$ and R$_8$ at each occurrence are independently H or CH$_3$;

R$_9$ is H or a straight or branched C$_1$-C$_6$ alkyl, preferably R$_9$ is H or —CH$_3$;

n is an integer from 0 to 6; preferably n is 0 or 1;

o is an integer from 1 to 6; preferably o is an integer from 2 to 4, more preferably o is 2;

p is an integer from 1 to 6; preferably p is an integer from 1 to 4; more preferably p is 1 or 2;

q is an integer from 0 to 6; preferably q is from 0 to 4, more preferably is 0 or 1;

X is O, S or NR$_{10}$ wherein R$_{10}$ is H or a C$_1$-C$_4$ alkyl; preferably X is O.

In another aspect of the invention, there is provided a compound of formula (I)

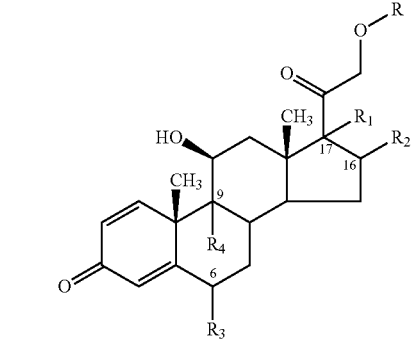

wherein

R$_1$ is OH, R$_2$ is CH$_3$, R$_3$ is a hydrogen atom and R$_4$ is F;

R$_1$ and R$_4$ are linked to the carbon atoms 17 and 9 of the steroidal structure in position α, R$_2$ is linked to the carbon atom 16 of the steroidal structure in position β;

R is:

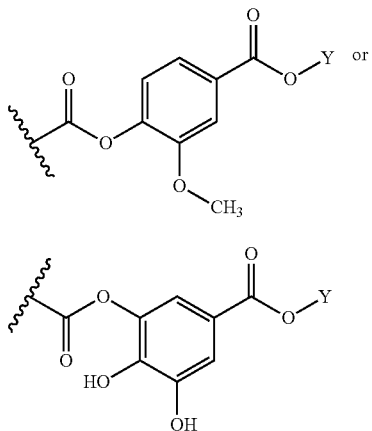

wherein
Y is selected from:
1) —$R_5$—CH(ONO$_2$)$R_6$
2) —$R_5$—CH(ONO$_2$)—(CR$_7$R$_8$)$_n$—CH(ONO$_2$)$R_9$
3) —[(CH$_2$)$_o$—X]$_p$—(CH$_2$)$_q$—CH(ONO$_2$)$R_9$
4) —[(CH$_2$)$_o$—(X)]$_p$—(CH$_2$)$_q$—CH(ONO$_2$)(CR$_7$R$_8$)$_n$—CH(ONO$_2$)$R_9$ wherein
$R_5$ is a straight or branched $C_1$-$C_{10}$ alkylene; preferably $R_5$ is a straight $C_1$-$C_6$ alkylene;
$R_6$ is H or a straight or branched $C_1$-$C_6$ alkyl, preferably $R_6$ is H or —CH$_3$;
$R_7$ and $R_8$ at each occurrence are independently H or a straight or branched $C_1$-$C_6$ alkyl; preferably $R_7$ and $R_8$ at each occurrence are independently H or CH$_3$;
$R_9$ is H or a straight or branched $C_1$-$C_6$ alkyl, preferably $R_9$ is H or —CH$_3$;
n is an integer from 0 to 6; preferably n is 0 or 1;
o is an integer from 1 to 6; preferably o is an integer from 2 to 4, more preferably o is 2;
p is an integer from 1 to 6; preferably p is an integer from 1 to 4; more preferably p is 1 or 2;
q is an integer from 0 to 6; preferably q is from 0 to 4, more preferably is 0 or 1;
X is O, S or NR$_{10}$ wherein R$_{10}$ is H or a $C_1$—O, alkyl; preferably X is O.

In another aspect of the invention, there is provided a compound of formula (I)

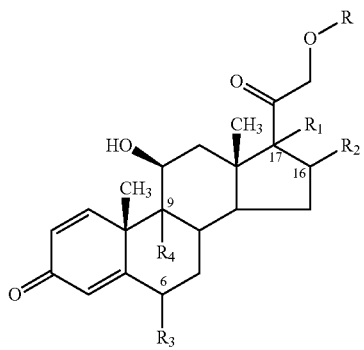

wherein
$R_1$ is OH, $R_2$ is CH$_3$, $R_3$ is a hydrogen atom and $R_4$ is Cl;
$R_1$ and $R_4$ are linked to the carbon atoms 17 and 9 of the steroidal structure in position α, $R_2$ is linked to the carbon atom 16 of the steroidal structure in position β;
R is:

(III)

(IV)

wherein
Y is selected from:
1) —$R_5$—CH(ONO$_2$)$R_6$
2) —$R_5$—CH(ONO$_2$)—(CR$_7$R$_8$)$_n$—CH(ONO$_2$)$R_9$
3) —[(CH$_2$)$_o$—X]$_p$—(CH$_2$)$_q$—CH(ONO$_2$)$R_9$
4) [(CH$_2$)$_o$—(X)]$_p$—(CH$_2$)$_q$—CH(ONO$_2$) (CR$_7$R$_8$)$_n$—CH(ONO$_2$)$R_9$ wherein
$R_5$ is a straight or branched $C_1$-$C_{10}$ alkylene; preferably $R_5$ is a straight $C_1$-$C_6$ alkylene;
$R_6$ is H or a straight or branched $C_1$-$C_6$ alkyl, preferably $R_6$ is H or —CH$_3$;
$R_7$ and $R_8$ at each occurrence are independently H or a straight or branched $C_1$-$C_6$ alkyl; preferably $R_7$ and $R_8$ at each occurrence are independently H or CH$_3$;
$R_9$ is H or a straight or branched $C_1$-$C_6$ alkyl, preferably $R_9$ is H or —CH$_3$;
n is an integer from 0 to 6; preferably n is 0 or 1;
o is an integer from 1 to 6; preferably o is an integer from 2 to 4, more preferably o is 2;
p is an integer from 1 to 6; preferably p is an integer from 1 to 4; more preferably p is 1 or 2;
q is an integer from 0 to 6; preferably q is from 0 to 4, more preferably is 0 or 1;
X is O, S or NR$_{10}$ wherein R$_{10}$ is H or a $C_1$-$C_4$ alkyl; preferably X is O.

Preferred R are:

(IIIa)

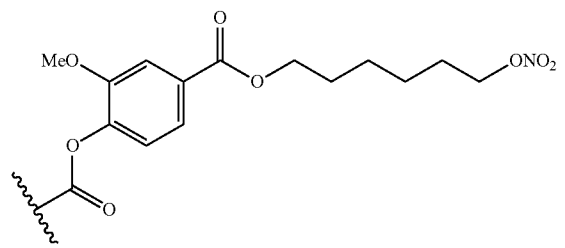
(IIIb)
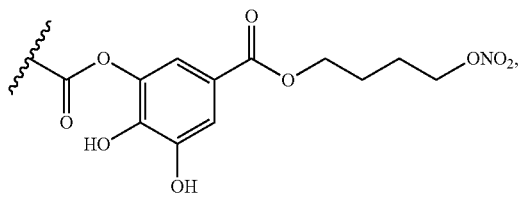
(IVa)
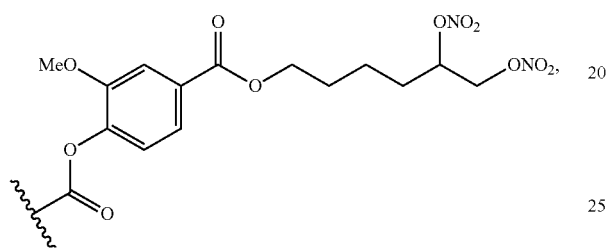
(IIIc)
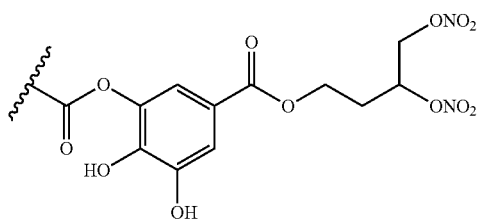
(IVb)
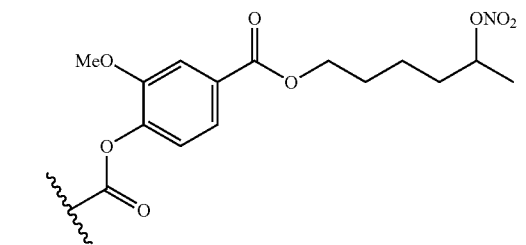
(IIId)
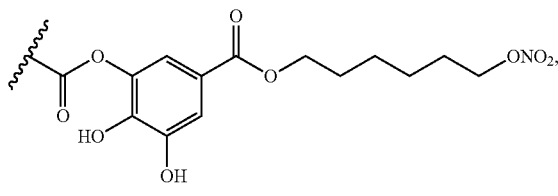
(IVc)
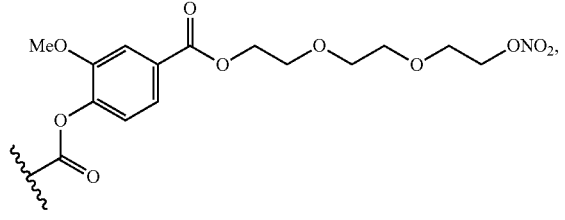
(IIIe)
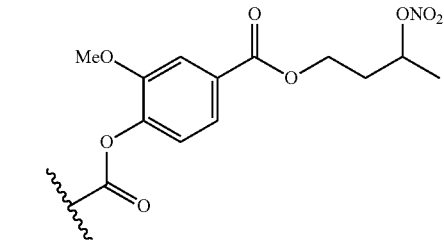
(IIIf)
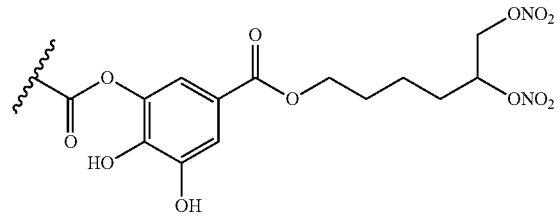
(IVd)
In another aspect of the invention, there is provided a compound selected from the following group:

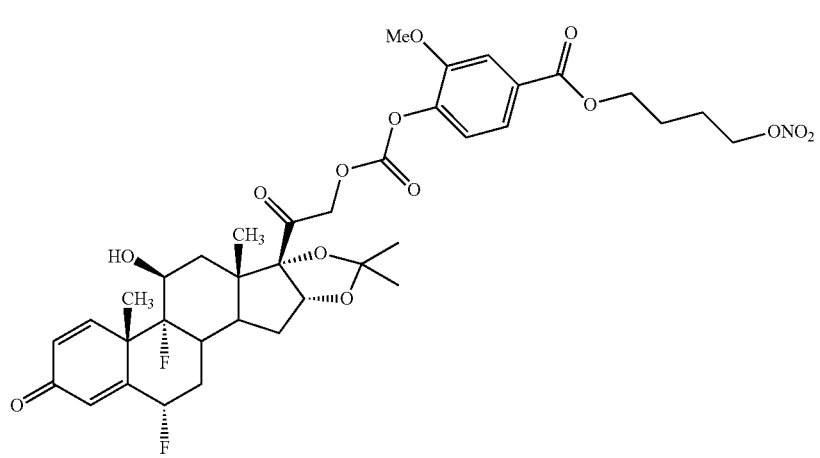
(1)
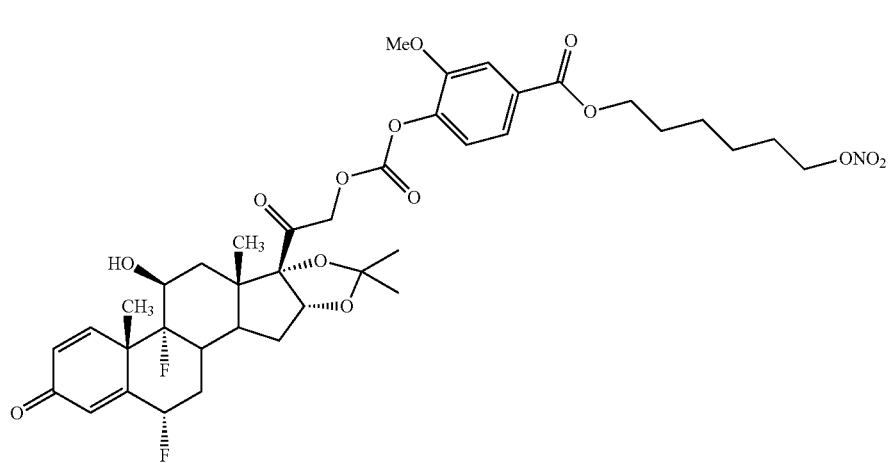
(2)
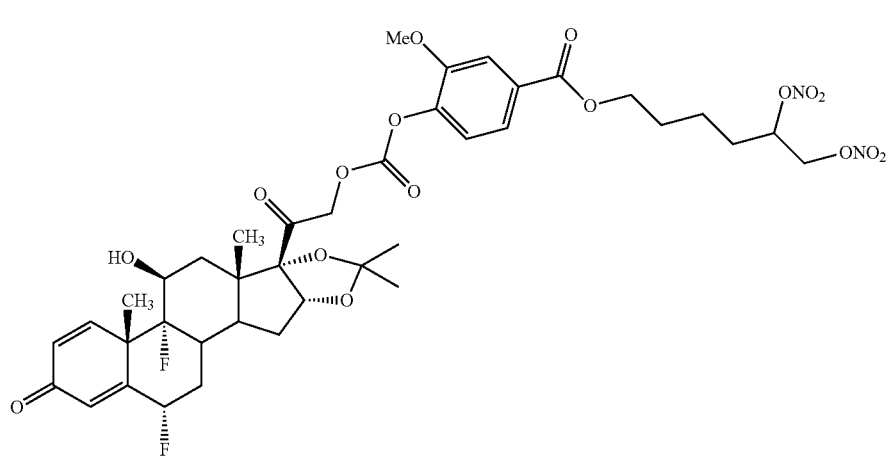
(3)

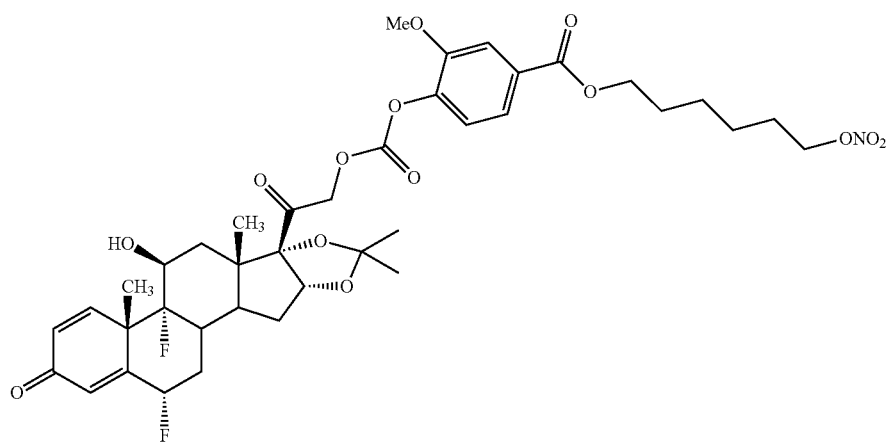
(4)
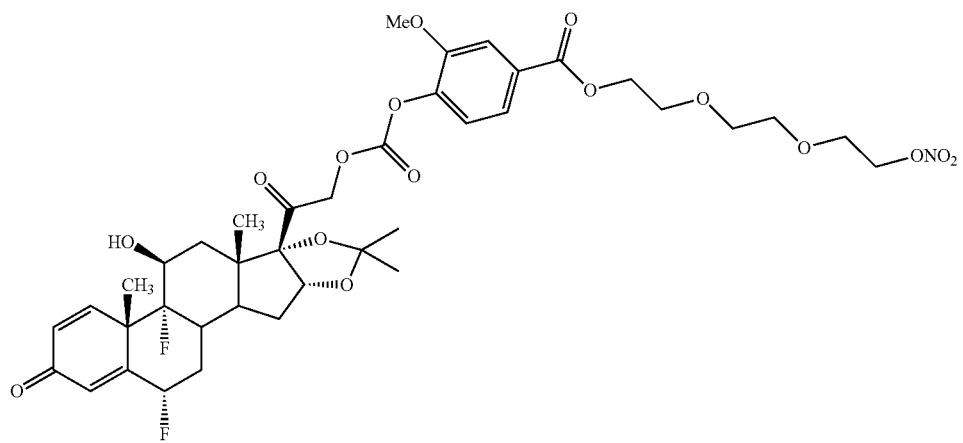
(5)
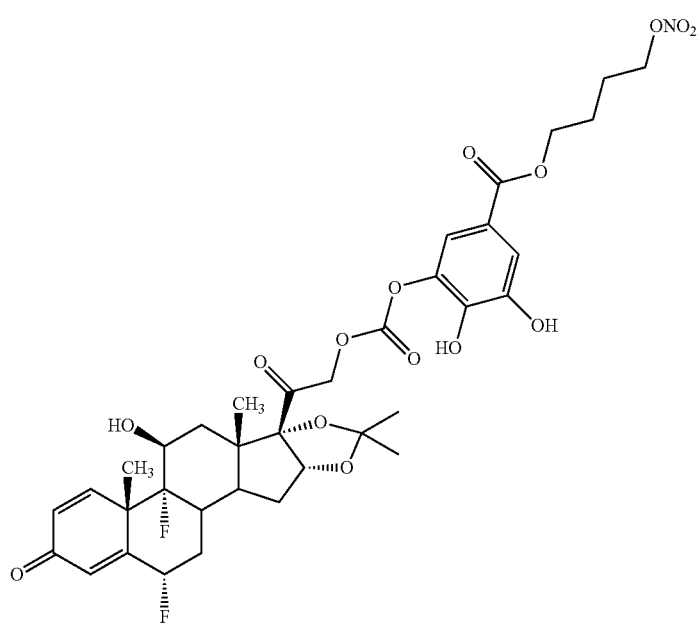
(6)

-continued
(7)
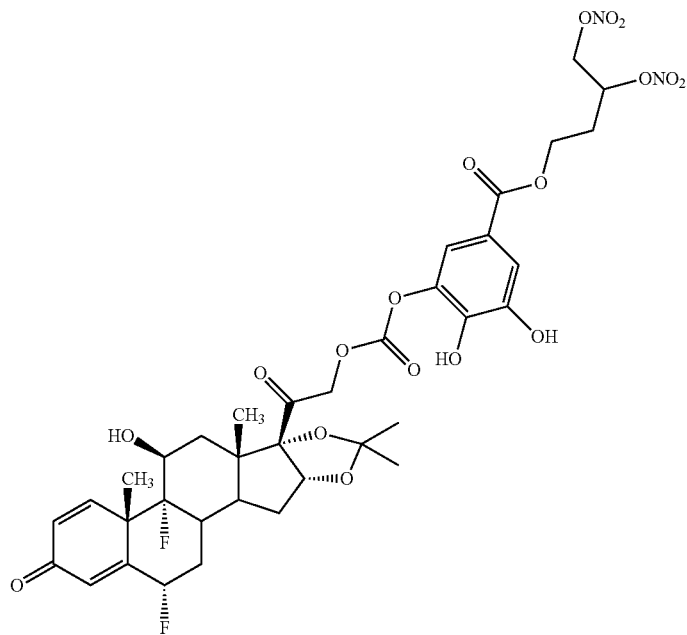
(8)
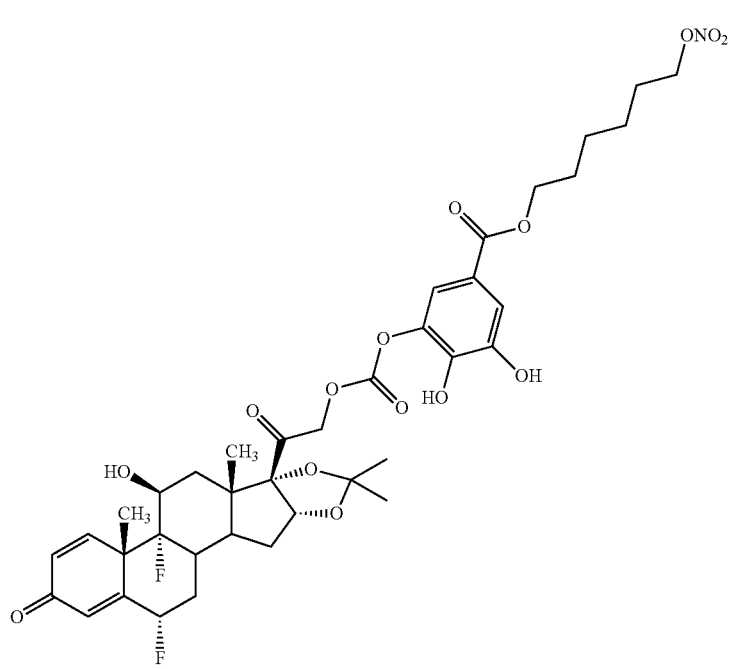

-continued
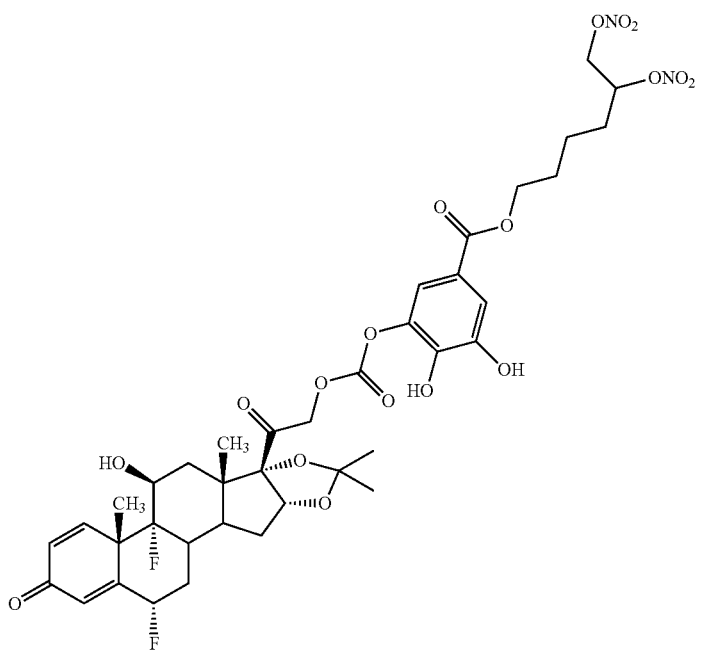
(9)
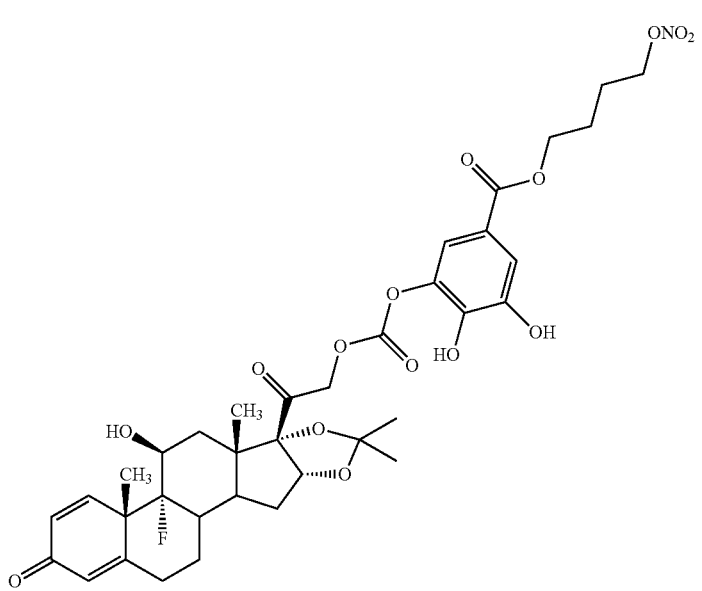
(10)

(11)
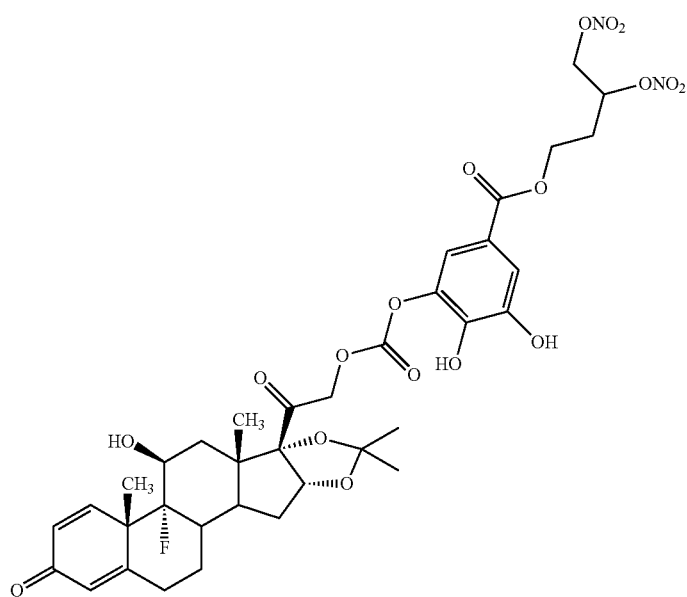
(12)
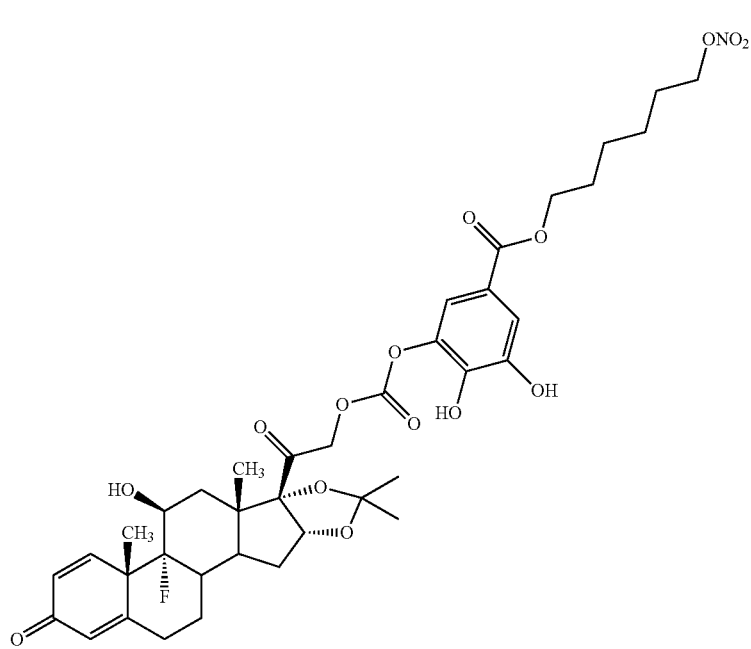

-continued
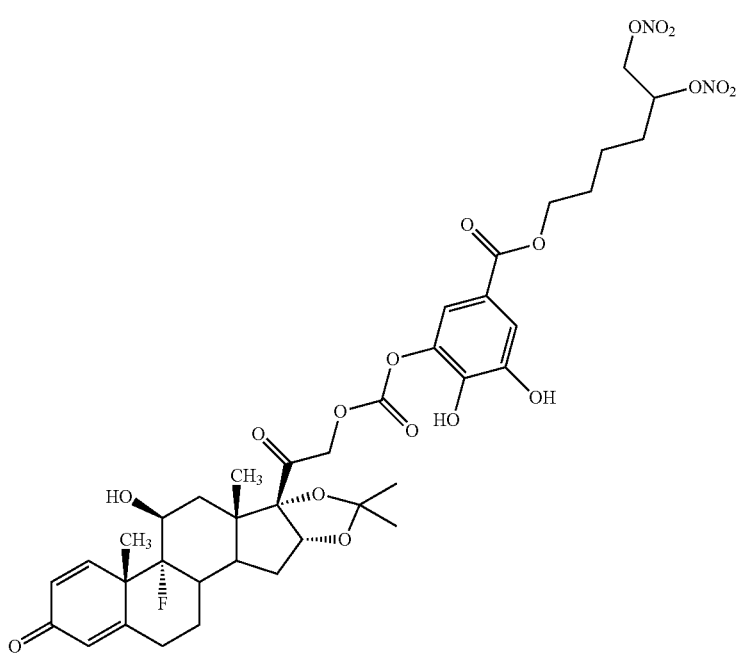
(13)
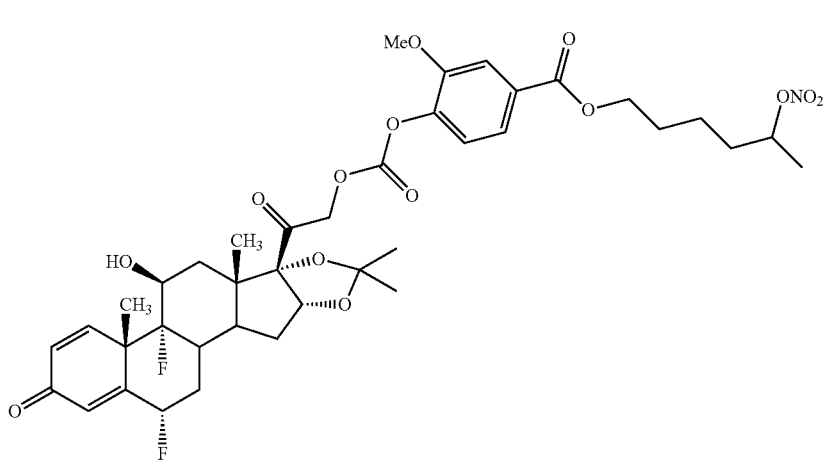
(14)
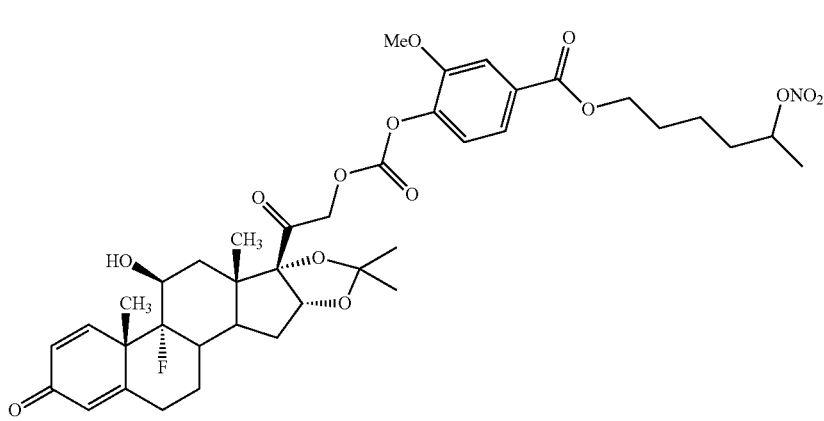
(15)

-continued (16)

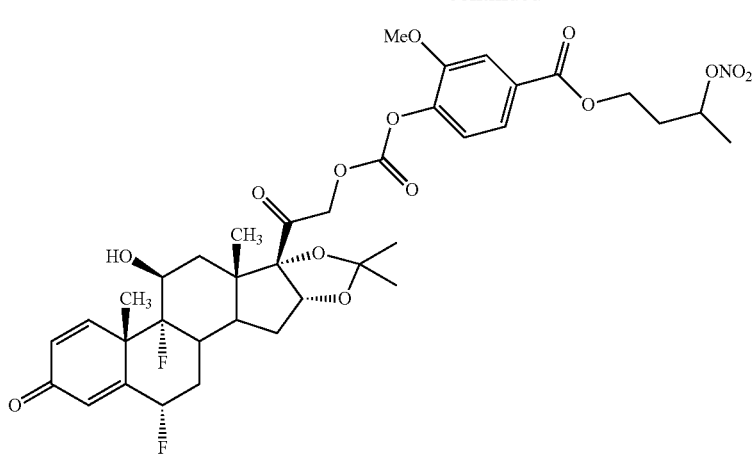

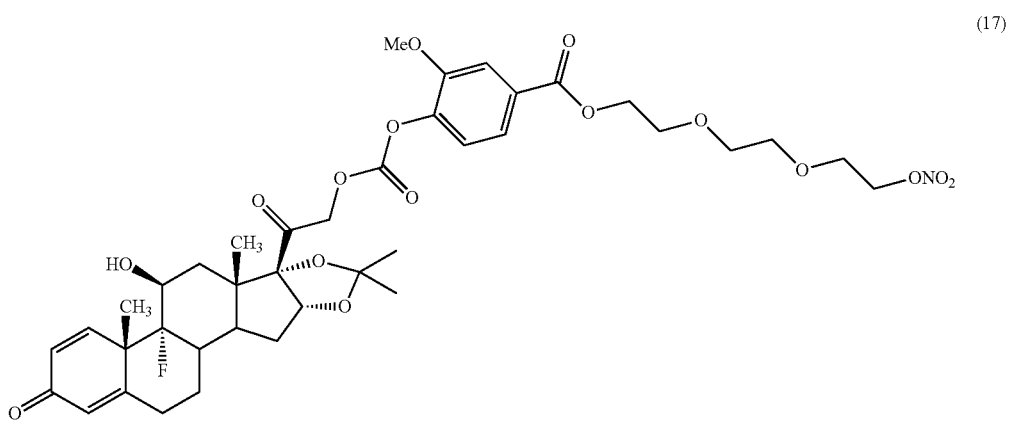

(17)

In another aspect of the invention, there is provided a compound of formula (I) for treating inflammatory diseases.

In another aspect of the invention, there is provided a compound of formula (I) for treating ocular diseases, in particular diabetic macular edema, diabetic retinopathy, macular degeneration, age-related macular degeneration and other diseases of retina and macula lutea. A preferred compound is the compound of formula (1) above reported.

In another aspect of the invention, there is provided a compound of formula (I) including the compounds of formula (I) wherein $R_1$ and $R_2$ taken together are the group of formula (II)

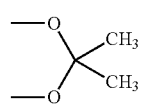

(II)

$R_4$ is F and $R_3$ is a hydrogen atom, and R is the compound of formula (III) wherein and Y is $-R_5-CH(ONO_2)R_6$ and $R_6$ is H, for the use in the prevention or in the treatment of diabetic macular edema, diabetic retinopathy, macular degeneration, age-related macular degeneration and other diseases of retina and macula lutea, in particular diabetic macular edema. A preferred compound is the compound of formula (18)

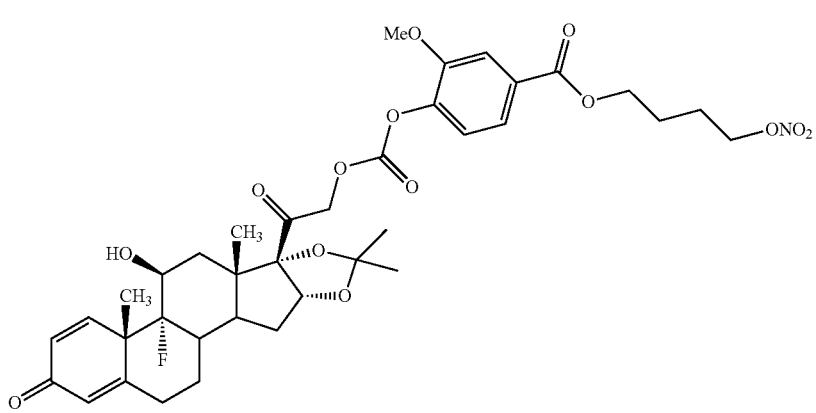

(18)

In yet another aspect of the invention, there is provided a pharmaceutical composition comprising a pharmaceutically effective amount of a compound of formula (I) and/or a salt or stereoisomer thereof and at lest an ophthalmically acceptable excipient in a suitable form for intravitreal or periorbital administration.

The term "excipient" is used herein to describe any ingredient other than the compound(s) of the invention. The choice of the excipient will to a large extent depend on factors such as the particular mode of administration, the effect of the excipient on the stability, and the nature of the dosage form.

In still another aspect of the invention, there is provided a pharmaceutical composition wherein the compound of the invention is administered as a suspension or emulsion in an ophthalmically acceptable vehicle.

The compounds of the invention intended for pharmaceutical use may be administered as crystalline or amorphous products. The compounds of the invention intended for pharmaceutical use may be administered alone or in combination with one or more other compounds of the invention.

The utility of the compounds of the invention as medical agents for the treatment or prevention of diabetic macula edema, diabetic retinopathy, macular degeneration, age-related macular degeneration and other diseases of retina and macula lutea is demonstrated by the activity of the compounds in conventional assays.

SYNTHESIS PROCEDURE

1) The compound of general formula (I) wherein $R_1$, $R_2$, $R_3$ and $R_4$ are as above defined, the radical R is as defined in formulae III and IV wherein Y is as above defined, can be obtained:
1.1) by reacting a compound of formula (V),

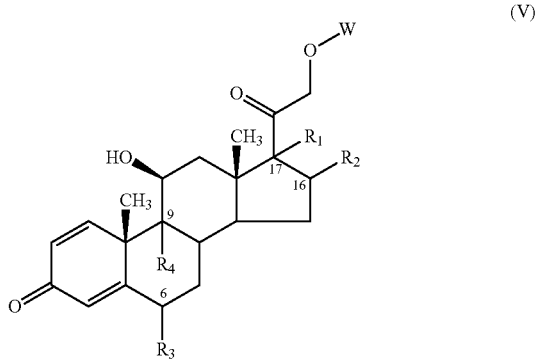

(V)

wherein $R_1$, $R_2$, $R_3$, $R_4$ are as above defined, W is H or C(O)—Cl with a compound of formula (VII) or (VIII)

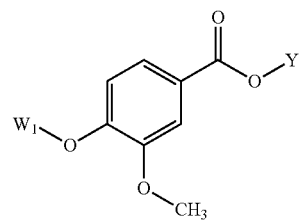

(VII)

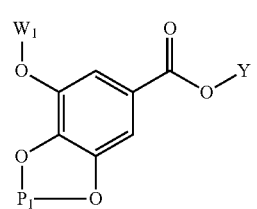

(VIII)

wherein Y is as above defined and
$W_1$ is H when W is —C(O)—Cl or
$W_1$ is —C(O)—Cl or —CO—O—$R_a$ when W is H, wherein $R_a$ is pentafluorophenyl or 4-nitrophenyl, $P_1$ is a diol protecting group such as acetal, such as p-methoxybenzylidene, butylidene, and those described in T. W. Greene "Protective groups in organic synthesis", Harvard University Press, 1980, $2^{nd}$ edition.

1.1.a) the reaction of a compound of formula (V) wherein W is H with a compound of formula (VII) or (VIII) wherein $W_1$ is —O(O)—Cl, or
the reaction of a compound of formula (V) wherein W is —C(O)—Cl with a compound of formula (VII) or (VIII) wherein $W_1$ is H, may be carried out in presence of an organic base such as N,N-dimethylamino pyridine (DMAP), triethylamine, pyridine. The reaction is carried out in an inert organic solvent such as N,N'-dimethylformamide, tetrahydrofuran, benzene, toluene, dioxane, a polyhalogenated aliphatic hydrocarbon at a temperature from −20° C. and 40° C. The reaction is completed within a time range from 30 minutes to 36 hours 1.1.b) the reaction of a compound of formula (V) wherein W is H with a compound of formula (VII) or (VIII) wherein $W_1$ is —C(O) —O—$R_a$, wherein $R_a$ is as above defined, may be carried out in presence of a catalyst, such as DMAP or in the presence of DMAP and a Lewis acid such as Sc(OTf)$_3$ or Bi(OTf)$_3$. The reaction is carried out in an inert organic solvent such as N,N'-dimethylformamide, tetrahydrofuran, benzene, toluene, dioxane, a polyhalogenated aliphatic hydrocarbon at a temperature from −20° C. and 40° C. The reaction is completed within a time range from 30 minutes to 36 hours;

1.2) optionally deprotecting the compounds obtained in step 1.1.a) or 1.1.b) according to methods described in T. W. Greene "Protective groups in organic synthesis", Harvard University Press, 1980, 2$^{nd}$ edition. Hydrochloric acid in tetrahydrofurane is the preferred method for removing acetal protecting group.

Preparation of the Compounds of Formula (V)

2) The compounds of formula (V) wherein:
W is H and R$_1$ is OH, R$_2$ is CH$_3$, R$_3$ is a hydrogen atom, R$_4$ is F or Cl;
or W is H, R$_3$ is a hydrogen atom or F, R$_4$ is F and R$_1$ and R$_2$ taken together are the group of formula (II)

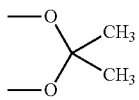

(II)

are commercially available.

2.1) The compounds of formula (V) wherein W is —C(O)—Cl or —CO—O—R$_a$ and R$_1$, R$_2$, R$_3$ and R$_4$ are as above defined can be obtained from the corresponding commercially available compounds of formula (V) wherein W is H using methods known in the literature.

Preparation of the Compounds of Formula (VII) or (VIII)

3) The compounds of formula (VII) or (VIII) wherein W$_1$ is H, P$_1$ is as above defined and
Y is:

—R$_5$—CH(ONO$_2$)R$_6$

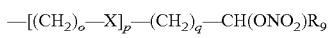

—[(CH$_2$)$_o$—X]$_p$—(CH$_2$)$_q$—CH(ONO$_2$)R$_9$ wherein R$_5$, R$_6$, R$_9$, o, p and q are as above defined can be prepared as follows:

3.1.a) by reacting a compound of formula (IX) or (X),

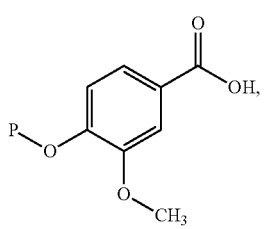

(IX)

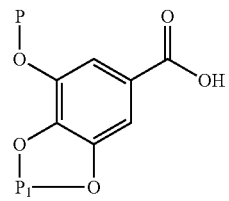

(X)

wherein P is a hydroxyl protecting group such as silyl ethers, such as trimethylsilyl, tert-butyl-dimethylsilyl or trityl and those described in T. W. Greene "Protective groups in organic synthesis", Harvard University Press, 1980 2$^{nd}$ edition, P$_1$ is as above reported,
with a compound of formula (XI) or (XII)

HO—R$_5$—CH(Q)R$_6$ or (XI)

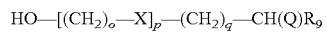

HO—[(CH$_2$)$_o$—X]$_p$—(CH$_2$)$_q$—CH(Q)R$_9$ (XII)

wherein R$_5$, R$_6$, R$_9$, o, p and q are as above defined and Q is ONO$_2$ or Q$_1$, wherein Q$_1$ is a chlorine atom, a bromine atom, a iodine atom, a mesyl group or a tosyl group,
in the presence of a condensing agent such as dicyclohexylcarbodiimide (DCC), N'-(3-dimethylaminopropyl)-N-ethylcarbodiimide hydrochloride (EDAC), N,N'-carbonyldiimidazole (CDI), optionally in the presence of a base, for example DMAP.
The reaction is carried out in an inert organic solvent dry such as N,N'-dimethylformamide, tetrahydrofuran, benzene, toluene, dioxane, a polyhalogenated aliphatic hydrocarbon at a temperature from −20° C. and 50° C. The reaction is completed within a time range from 30 minutes to 36 hours;

3.1.b) by reacting a compound of formula (IX) or (X) as above reported
with a compound of formula (XIII) or (XIV)

W$_3$—R$_5$—CH(Q)R$_6$ or (XIII)

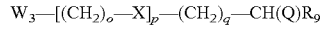

W$_3$—[(CH$_2$)$_o$—X]$_p$—(CH$_2$)$_q$—CH(Q)R$_9$ (XIV)

wherein R$_5$, R$_6$, R$_9$, o, p, q and Q are as above defined and W$_3$ is Cl, Br, I,
in the presence of a organic base such as 1,8-diazabiciclo[5.4.0]undec-7-ene (DBU), N,N-diisopropylethyl amine, diisopropylamine or an inorganic base such as alkaline-earth metal carbonate or hydroxide, potassium carbonate, cesium carbonate, in an inert organic solvent such as N,N'-dimethylformamide, tetrahydrofuran, acetone, methyl ethyl ketone, acetonitrile, a polyhalogenated aliphatic hydrocarbon at a temperature from −20° C. and 40° C., preferably from 5° C. to 25° C. The reaction is completed within a time range from 1 to hours. When W$_3$ is chosen among chlorine or bromine the reaction is carried out in presence an iodine salts such as KI.

3.1.c) by reacting a compound of formula (IXa) or (Xa)

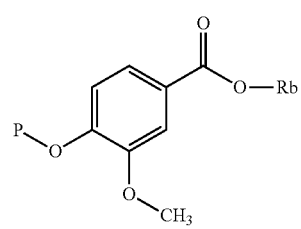

(IXa)

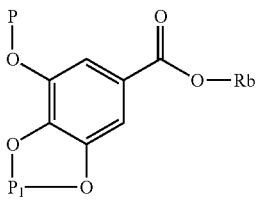
(Xa)

wherein P and P$_1$ are as above defined, and R$_b$ is pentafluorophenyl, 4-nitrophenyl, or —(N-succimidyl), with a compound of formula (XI) or (XII)

HO—R$_5$—CH(Q)R$_6$ or (XI)

HO—[(CH$_2$)$_o$—X]$_p$—(CH$_2$)$_q$—CH(Q)R$_9$ (XII)

wherein R$_5$, R$_6$, R$_9$, o, p, q and Q are as above defined, in the presence of a catalyst, such as DMAP or in the presence of DMAP and a Lewis acid such as Sc(OTf)$_3$ or Bi(OTf)$_3$.

The reaction is carried out in an inert organic solvent such as N,N'-dimethylformamide, tetrahydrofuran, benzene, toluene, dioxane, a polyhalogenated aliphatic hydrocarbon at a temperature from –20° C. and 40° C. The reaction is completed within a time range from 30 minutes to 36 hours;

3.1.d) by reacting a compound of formula (IXb) or (Xb)

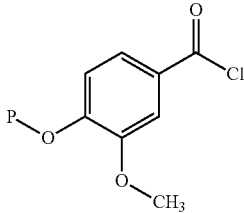
(IXb)

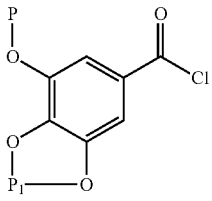
(Xb)

with a compound of formula (XI) or (XII)

HO—R$_5$—CH(Q)R$_6$ or (XI)

HO—[(CH$_2$)$_o$—X]$_p$—(CH$_2$)$_q$—CH(Q)R$_9$ (XII)

wherein R$_5$, R$_6$, R$_9$, o, p, q and Q are as above defined, in the presence of an organic base such as N,N-dimethylamino pyridine (DMAP), triethylamine, pyridine. The reaction is carried out in an inert organic solvent such as N,N'-dimethylformamide, tetrahydrofuran, benzene, toluene, dioxane, a polyhalogenated aliphatic hydrocarbon at a temperature from –20° C. and 40° C. The reaction is completed within a time range from 30 minutes to 36 hours.

3.2) by reacting the compound obtained in the steps 3.1.a)-3.1.d) wherein Q is Q$_1$, with a nitrate source such as silver nitrate, lithium nitrate, sodium nitrate, potassium nitrate, magnesium nitrate, calcium nitrate, iron nitrate, zinc nitrate or tetraalkylammonium nitrate (wherein alkyl is C$_1$-C$_{10}$ alkyl) in a suitable organic solvent such as acetonitrile, tetrahydrofurane, methyl ethyl ketone, ethyl acetate, DMF, the reaction is carried out, in the dark, at a temperature from room temperature to the boiling temperature of the solvent. Alternatively the reaction with AgNO$_3$ can be performed under microwave irradiation in solvents such acetonitrile or THF at temperatures in the range between about 100-180° C. for time range about 1-60 min. Preferred nitrate source is silver nitrate and 3.3) optionally removing the hydroxyl protective group P according to the methods described in T. W. Greene "Protective groups in organic synthesis", Harvard University Press, 1980, 2$^{nd}$ edition. Fluoride ion is the preferred method for removing the silyl ether group.

4) The compounds of formula (VII) or (VIII) wherein W$_1$ is H, P$_1$ is as above defined and Y is —R$_5$—CH(ONO$_2$)—(CR$_7$R$_8$)$_n$—CH(ONO$_2$)R$_9$

[(CH$_2$)$_o$—X]$_p$—(CH$_2$)$_q$—CH(ONO$_2$)—(CR$_7$R$_8$)$_n$—CH(ONO$_2$)R$_9$ wherein R$_5$, R$_9$, R$_7$, R$_8$, o, p and q are as above defined and n is 0 can be prepared as follows:

4.1.a) by reacting a compound of formula (IX) or (X) as above reported, with a compound of formula (XV) or (XVI)

HO—R$_5$—CH=CH—R$_9$ (XV)

HO—[(CH$_2$)$_o$—X]$_p$—(CH$_2$)$_q$—CH=CH—R$_9$ (XVI)

wherein R$_5$, o, p, q, X and R$_9$ are as above defined, according to the method described in 3.1.a);

4.1.b) by reacting a compound of formula (IX) or (X) as above reported, with a compound of formula (XVII) or (XVIII)

W$_3$—R$_5$—CH=CH—R$_9$ (XVII)

W$_3$—[(CH$_2$)$_o$—X]$_p$—(CH$_2$)$_q$—CH=CH—R$_9$ (XVIII)

wherein R$_5$, o, p, q, X and R$_9$ are as above defined and W$_3$ is Cl, Br, I, according to the method described in 3.1.b)

4.1.c) by reacting a compound of formula (IXa) or (Xa) as above reported, with a compound of formula (XV) or (XVI)

HO—R$_5$—CH=CH—R$_9$ (XV)

HO—[(CH$_2$)$_o$—X]$_p$—(OH$_2$)$_q$—CH=CH—R$_9$ (XVI)

wherein R$_5$, o, p, q, X and R$_9$ are as above defined, according to the method described in 3.1.c)

4.1.d) by reacting a compound of formula (IXb) or (Xb) as above reported with a compound of formula (XV) or (XVI)

HO—R$_5$—CH=CH—R$_9$ (XV)

HO—[(CH$_2$)$_o$—X]$_p$—(CH$_2$)$_q$—CH=CH—R$_9$ (XVI)

wherein R$_5$, o, p, q, X and R$_9$ are as above defined, according to the method described in 3.1.d)

4.2.a) by reacting a compound of formula (VIIA) or (VIIIA)

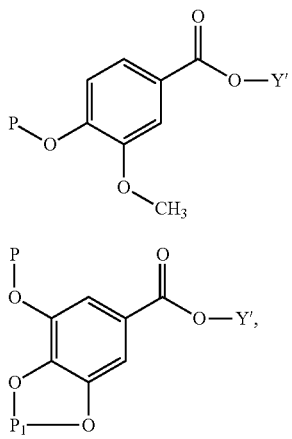

wherein P and P$_1$ are as above defined
and Y' is:

—R$_5$—CH=CH—R$_9$

—[(CH$_2$)$_o$—X]$_p$—(CH$_2$)$_q$—CH=CH—R$_9$ wherein R$_5$, o, p, q and R$_9$ are as above defined,
with a nitrate source such as silver nitrate, in presence of iodine in a suitable organic solvent such as acetonitrile, tetrahydrofurane, methyl ethyl ketone, ethyl acetate, DMF, the reaction is carried out, in the dark, at a temperature from −20° C. to the boiling temperature of the solvent. Alternatively the reaction can be performed under microwave irradiation in solvents such acetonitrile or THF at temperatures in the range between about 100-180° C. for time range about 1-60 min.

Alternatively 4.2.b) by dihydroxylation of the double bond of the compound of formula (VIIA) or (VIIIA) above defined to obtain a compound (VIIB) or (VIIIB)

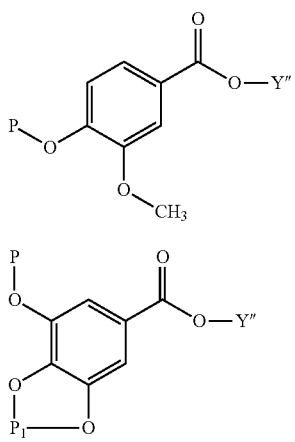

wherein P and P$_1$ are as above defined
and Y'' is:

—R$_5$—CH(OH)—CH(OH)—R$_9$

—[(CH$_2$)$_o$—X]$_p$—(CH$_2$)$_q$—CH(OH)—CH(OH)—R$_9$ wherein R$_5$, o, p, q and R$_9$ are as above defined,
with a reagent for Sharpless asymmetric dihydroxylation such as ADmix alpha or ADmix beta in a mixture water/tert-butanol, at a temperature from −20° C. and 30° C., preferably from −5° C. to 5° C. The reaction is completed within a time range from 1 to 24 hours.

4.3) by reacting the compound obtained in the steps 4.2.b) with nitric acid and acetic anhydride in a suitable organic solvent such as methylene chloride, in a temperature range from −50° C. to 0° C. according to methods well known in the literature.

4.4) optionally deprotecting the compounds obtained in step 4.2.a) or 4.3) as described in T. W. Greene "Protective groups in organic synthesis", Harvard University Press, 1980, 2$^{nd}$ edition. Fluoride ion is the preferred method for removing silyl ether protecting group.

5) The compounds of formula (VII) or (VIII) wherein W$_1$ is H, P$_1$ is as above defined and Y is —R$_5$—CH(ONO$_2$)$_n$—(CR$_7$R$_8$)$_n$—CH(ONO$_2$)R$_9$

[(CH$_2$)$_o$—X]$_p$—(CH$_2$)$_q$—CH(ONO$_2$)—(CR$_7$R$_8$)$_n$—CH(ONO$_2$)R$_9$ wherein R$_5$, R$_9$, R$_7$, R$_8$, o, p and q are as above defined and n is an integer from 1 to 6
can be prepared as follows:

5.1) by reacting a compound of formula (IX) or (X) as above reported
with a compound of formula (XIX) or (XX)

W$_3$—R$_5$—CH(Q$_2$)—(CR$_7$R$_8$)$_n$—CH(Q$_2$)R$_9$ or (XIX)

W$_3$—[(CH$_2$)$_o$—X]$_p$—(CH$_2$)$_q$—CH(Q$_2$)—(CR$_7$R$_8$)$_n$—CH(Q$_2$)R$_9$ (XX)

wherein R$_5$, R$_9$, R$_7$, R$_8$, n, o, p and q are as above defined, Q$_2$ is ONO$_2$ or OH and W$_3$ is Cl, Br, I,
according to the method described in 3.1.b);

5.2) by reacting the compound obtained in the steps 5.1) wherein Q is OH, with a nitrate source according to the method described in 4.3);

5.3) optionally removing the hydroxyl protective group P according to the method described in 3.3);

Preparation of Compounds (IX), (IXa), (IXb), (X), (Xa) and (Xb)

5) The compounds of formula (IX), (IXa), (IXb), (X), (Xa) and (Xb) wherein P, P$_1$ and R$_b$ are as above described, can be prepared starting from vanillic acid or gallic acid, which are commercially available, according to method known in the literature.

Preparation of Compounds (XI)-(XX)

6.1) The compounds of formula (XI)-(XIV) wherein R$_5$, R$_6$, R$_9$, o, p, q and W$_3$ are as above defined and Q is Q$_1$ wherein Q$_1$ is as above defined, are commercially available or can be obtained according methods known in the literature.

6.2) The compounds of formula (XI)-(XIV) wherein R$_5$, R$_6$, R$_9$, o, p, q and W$_3$ are as above defined and Q is ONO$_2$ can be obtained from the corresponding compounds wherein Q is Q$_1$ by reaction with a nitrate source as above described.

6.3) The compounds of formula (XV)-(XX) wherein W$_3$, R$_5$, R$_9$, R$_7$, R$_8$, n, o, p and q are as above defined, are commercially available or can be obtained according to methods known in the literature.

EXAMPLE 1

Compound (1)

Synthesis of 4-(nitrooxy)butyl 4-((2-((6S,9R,10S,11S,13S,16R,17S)-6,9-difluoro-11-hydroxy-16,17-16,17-(1-methylethylidenebis(oxy))-10,13-dimethyl-3-oxo-6,7,8,9,10,11,12,13,14,15,16,17-dodecahydro-3H-cyclopenta[a]phenanthren-17-yl)-2-oxoethoxy)carbonyloxy)-3-methoxybenzoate

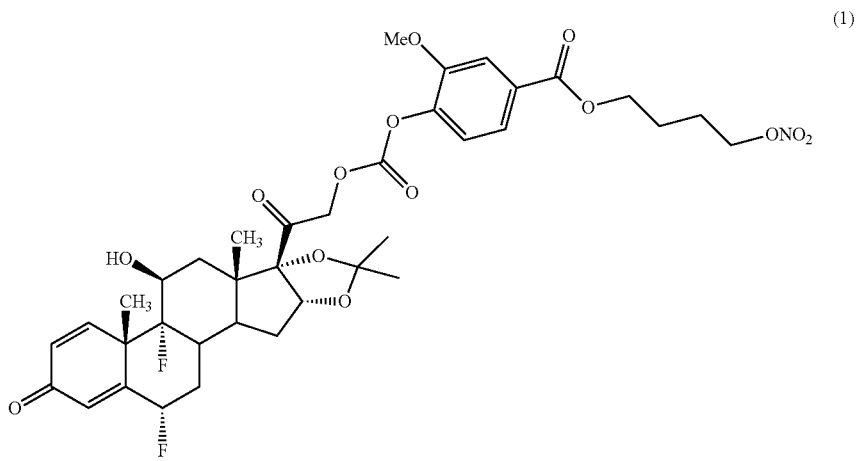

A) 4-(Nitrooxy)butyl 4-hydroxy-3-methoxybenzoate

B) 4-(Nitrooxy)butyl-3-methoxy-4-((4-nitrophenoxy)carbonyloxy)benzoate

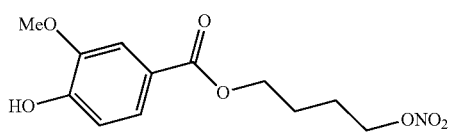

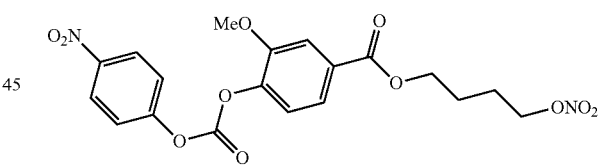

To a solution of vanillic acid (5.0 g, 29.73 mmol) in N,N-dimethylformamide (50 ml), cesium carbonate (9.68 g, 29.73 mmol) was added. The reaction was cooled at 0° C. and a 20% solution of 1-bromo-4-(nitrooxy)butane in dichloromethane (29.45 g) was added. The reaction was stirred at room temperature for 69 hours. The mixture was poured into a 5% aqueous $NaH_2PO_4$ solution and extracted with diethyl ether (3×70 ml) The organic layers were washed with water (70 ml), dried over sodium sulfate and concentrated under reduced pressure. The residue was purified by flash chromatography (Biotage System, Cartridge column FLASH 65+M™ KP-Sil, eluent: gradient n-hexane/ethyl acetate 95/5 (500 ml), to n-hexane/ethyl acetate 1/1 during 4000 ml, n-hexane/ethyl acetate 1/1 (500 ml)). The product (5.88 g) was obtained.

To a solution of compound A (2.94 g, 10.30 mmol) in dichloromethane (50 ml), cooled at 0° C., pyridine (1.01 ml, 10.30 mmol) and p-nitrophenyl chloroformate (2.07 ml, 10.30 mmol) were added. The reaction was stirred at room temperature for 16 hours. The mixture was washed with 1M aqueous HCl (2×50 ml), the organic layer was dried over sodium sulfate and concentrated under reduced pressure. The residue was purified by flash chromatography (Biotage System, Cartridge column FLASH 65+M™ KP-Sil, eluent: gradient n-hexane/ethyl acetate 93/7 (500 ml), to n-hexane/ethyl acetate 1/1 during 4000 ml, n-hexane/ethyl acetate 1/1 (500 ml)). The product (3.50 g) was obtained.

C) 4-(nitrooxy)butyl 4-((2-((6S,9R,10S,11S,13S,
16R,17S)-6,9-difluoro-1'-hydroxy-16,17-16,17-(1-
methylethylidenebis(oxy))-10,13-dimethyl-3-oxo-6,
7,8,9,10,11,12,13,14,15,16,17-dodecahydro-3H-
cyclopenta[a]phenanthren-17-yl)-2-oxoethoxy)
carbonyloxy)-3-methoxybenzoate To a solution of compound B (1.00 g, 2.28 mmol) in chloroform (30 ml), scandium triflate (0.10 g, 0.22 mmol) and DMAP (0.54 g, 4.56 mmol) were added. The reaction was cooled at 0° C. and fluocinolone acetonide (0.99 g, 2.28 mmol) was added. The reaction was stirred at room temperature for 28 hours. The mixture was diluted with dichloromethane (30 ml), washed with 5% NaH$_2$PO$_4$ and then with saturated aqueous sodium carbonate. The organic layer was dried over sodium sulfate and concentrated under reduced pressure. The residue was purified by flash chromatography, (Biotage System, column FLASH 40+M™ KP-Sil, eluent: gradient n-hexane/ethyl acetate 9/1 (200 ml), to n-hexane/ethyl acetate 3/7 during 2000 ml, n-hexane/ethyl acetate 3/7 (600 ml)). The product (0.29 g) was obtained.

The product was crystallized by n-hexane/ethyl acetate
M.p.=199-200° C.
$^1$H-NMR: (DMSO), δ: 7.65 (2H, d); 7.38 (1H, d); 7.27 (1H, d); 5.60 (1H, dm); 5.50 (1H, s); 5.35 (2H, m); 4.60 (2H, t); 4.35 (2H, t); 4.20 (1H, m); 3.89 (3H, s); 2.75-2.50 (2H, m); 2.25 (1H, m); 2.00 (2H, m); 1.90-1.30 (13H, m); 1.15 (3H, s); 0.83 (3H, s).

EXAMPLE 2

Compound (3)

Synthesis of 5,6-bis(nitrooxy)hexyl 4-((2-((6S,9R,
10S,11S,13S,16R,17S)-6,9-difluoro-11-hydroxy-16,
17-((1-methylethylidene)bis(oxy))-10,13-dimethyl-
3-oxo-6,7,8,9,10,11,12,13,14,15,16,17-dodecahydro-
3H-cyclopenta[a]phenanthren-17-yl)-2-oxoethoxy)
carbonyloxy)-3-methoxybenzoate D) Hex-5-enyl 4-hydroxy-3-methoxybenzoate

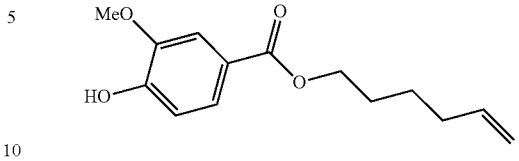

To a solution of vanillic acid (0.6 g, 3.56 mmol) in N,N-dimethylformamide (7 ml), diisopropylethylamine (0.93 ml, 5.35 mmol) and 6-bromohex-1-ene (0.71 ml, 5.35 mmol) were added. The reaction was stirred at 50° for 8 hours. The solvent was evaporated under vacuum. The residue was purified by flash chromatography (Biotage System, column FLASH 40+M™ KP-Sil, eluent: gradient n-hexane/ethyl acetate 95/5 (200 ml), to n-hexane/ethyl acetate 7/3 during 2000 ml, n-hexane/ethyl acetate 3/7 (400 ml)). The product (0.59 g) was obtained.

E) Hex-5-enyl
4-(tert-butyldimethylsilyloxy)-3-methoxybenzoate

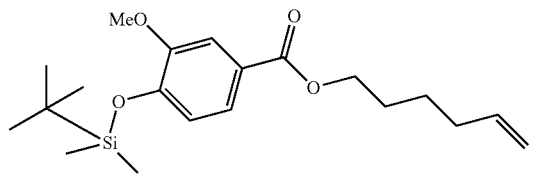

To a solution of compound D (1.16 g, 4.64 mmol) in N,N-dimethylformamide (30 ml), imidazole (1.18 g, 17.40 mmol) and tert-butyldimethylchlorosilane (1.31 g, 8.7 mmol) were added. The reaction was stirred at room temperature for 12 hours. The mixture was poured in water (50 ml) solution and extracted with diethyl ether (3×50 ml) The organic layers

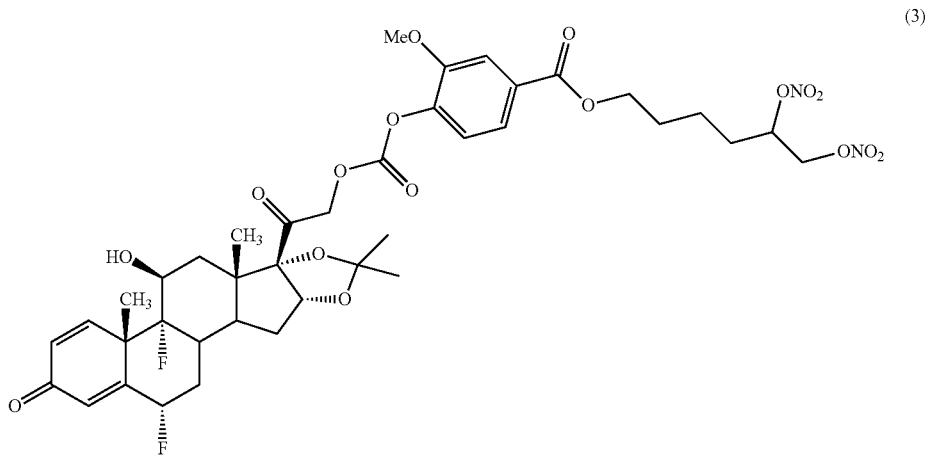

(3)

were dried over sodium sulfate and concentrated under reduced pressure. The residue was purified by flash chromatography (Biotage System, column FLASH 40+M™ KP-Sil, eluent: n-hexane/ethyl acetate 95/5. The product (1.56 g) was obtained.

F) 5,6-Bis(nitrooxy)hexyl-4-(tert-butyldimethylsilyloxy)-3-methoxybenzoate

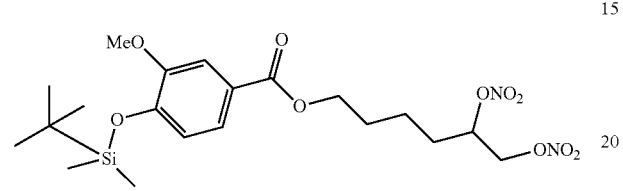

To a solution of compound E (1.4 g, 3.97 mmol) in acetonitrile (30 ml), silver nitrate (0.8 g, 4.77 mmol) was added. The reaction was cooled at −15° C. and iodine (1.21 g, 4.77 mmol) was added. The reaction was stirred at −15° C. for 20 minutes. The temperature was risen to 25° C. and iodine (2.7 g, 15.9 mmol) was added. The reaction was heated to 100° C. for 60 minutes under microwave irradiation. The resulting mixture was cooled, filtered and the solvent was removed under reduced pressure. The residue was purified by flash chromatography (Biotage System, column FLASH 40+M™ KP-Sil, eluent: gradient n-hexane/ethyl acetate 9/1 (400 ml), to n-hexane/ethyl acetate 7/3 during 2000 ml, n-hexane/ethyl acetate 7/3 (400 ml)). The product (1.19 g) was obtained.

G) 5,6-Bis(nitrooxy)hexyl 4-hydroxy-3-methoxybenzoate

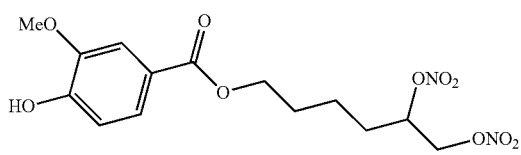

To a solution of compound F (1.19 g, 2.43 mmol) in tetrahydrofurane (40 ml) cooled at −0° C., a solution of tetrabutylamonium floride 1M in tetrahydrofurane (2.43 ml, 2.43 mmol) was added. The reaction was stirred at 0° C. for 20 minutes. The mixture was poured into a 5% aqueous $NaH_2PO_4$ solution and extracted with ethyl acetate (3×50 ml) The organic layers were washed with water (50 ml), dried over sodium sulfate and concentrated under reduced pressure. The residue was purified by flash chromatography (Biotage System, column FLASH 40+M™ KP-Sil, eluent: gradient n-hexane/ethyl acetate 9/1 (200 ml), to n-hexane/ethyl acetate 1/1 during 1000 ml, n-hexane/ethyl acetate 1/1 (200 ml), to n-hexane/ethyl acetate 4/6 during 200 ml, n-hexane/ethyl acetate 4/6 (400 ml)). The product (0.9 g) was obtained.

H) 2-((6S,9R,10S,11S,13S,16R,17S)-6,9-difluoro-11-hydroxy-16,17-((1-methylethylidene)bis(oxy))-10,13-dimethyl-3-oxo-6,7,8,9,10,11,12,13,14,15,16,17-dodecahydro-3H-cyclopenta [a]phenanthren-17-yl)-2-oxoethyl carbonochloridate

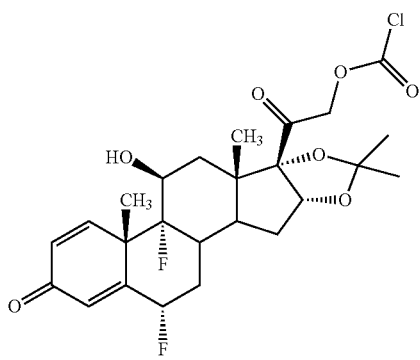

To a solution of fluocinolone acetonide (1.2 g, 2.65 mmol) in tetrahydrofurane (24 ml), cooled at 0° C. and under $N_2$, a 20% toluene solution of phosgene (5.58 ml, 10.6 mmol) was added. The reaction was stirred at 0° C. for 30 minutes and at room temperature for 12 hours. The excess of phosgene was removed by heating at 40° C. for 45 minutes. The solvent was evaporated under vacuum. The crude product was used in the next step without any purification.

I) 5,6-Bis(nitrooxy)hexyl 4-((2-((6S,9R,10S,11S, 13S,16R,17S)-6,9-difluoro-11-hydroxy-16,17-((1-methylethylidene)bis(oxy))-10,13-dimethyl-3-oxo-6, 7,8,9,10,11,12,13,14,15,16,17-dodecahydro-3H-cyclopenta[a]phenanthren-17-yl)-2-oxoethoxy) carbonyloxy)-3-methoxybenzoate To a solution of compound H (0.56 g, 1.09 mmol) in dichloromethane (24 ml), diisopropylethylamine (0.21 ml, 1.2 mmol) was added. The reaction was cooled at 0° C. and a solution of compound G (0.45 g, 1.2 mmol) in dichloromethane (3 ml) was added. The reaction was stirred at room temperature for 12 hours. The solvent was evaporated under vacuum. The residue was purified by flash chromatography (Biotage System, column FLASH 40+M™ KP-Sil, eluent: gradient n-hexane/ethyl acetate 8/2 (200 ml), to n-hexane/ethyl acetate 2/8 during 2400 ml, n-hexane/ethyl acetate 2/8 (400 ml)). The product (0.67 g) was obtained.

$^1$H-NMR: ($CDCl_3$), δ: 7.70 (2H, d); 7.30 (1H, d); 7.07 (1H, d); 6.45 (1H, s); 6.38 (1H, dd); 5.52-5.28 (2H, m); 5.16-4.91 (2H, dd); 5.04 (1H, d); 4.74 (1H, dd); 4.50 (1H, m); 4.43-4.35 (3H, m); 3.95 (3H, s); 2.60-2.10 (4H, m); 1.90-1.47 (16H, m); 1.25 (3H, s); 0.95 (3H, s).

EXAMPLE 3

Compound (5)

Synthesis of 2-(2-(2-(nitrooxy)ethoxy)ethoxy)ethyl 4-((2-(((6S,9R,10S,11S,13S,16R,17S)-6,9-difluoro-11-hydroxy-16,17-((1-methylethylidene)bis(oxy))-10,13-dimethyl-3-oxo-6,7,8,9,10,11,12,13,14,15,16,17-dodecahydro-3H-cyclopenta[a]phenanthren-17-yl)-2-oxoethoxy)carbonyloxy)-3-methoxybenzoate

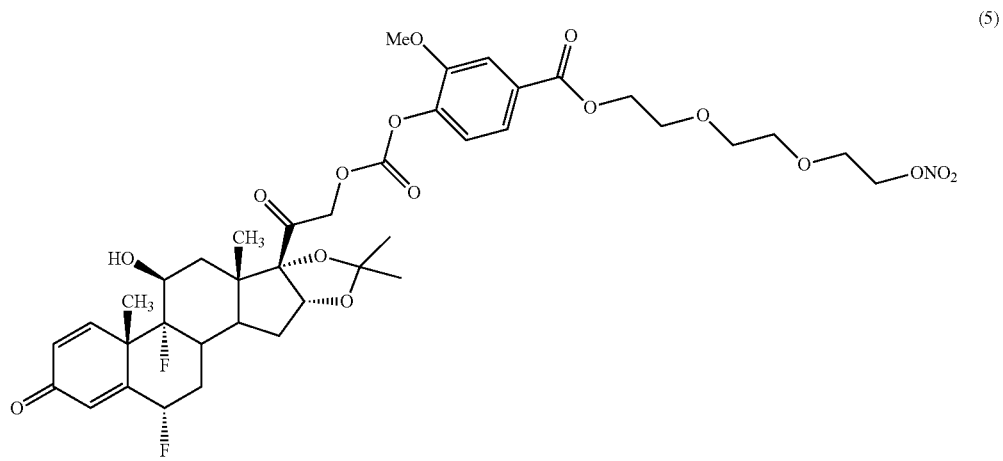

J) 4-(tert-butyldimethylsilyloxy)-3-methoxybenzoic acid

K) 2-(2-(2-chloroethoxy)ethoxy)ethyl-4-(tert-butyldimethyl silyloxy)-3-methoxybenzoate

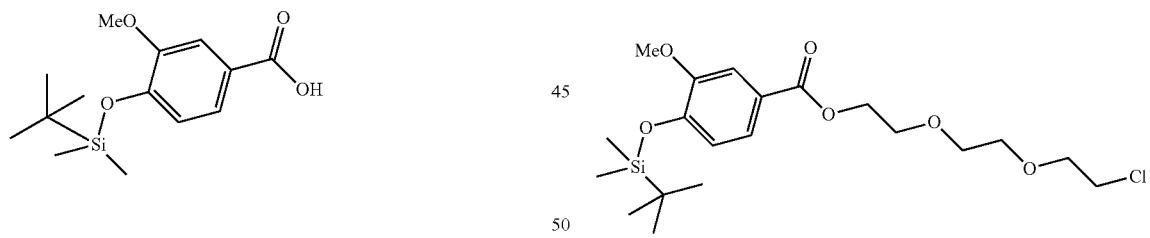

To a solution of vanillic acid (2.0 g, 11.89 mmol) in N,N-dimethylformamide (50 ml), imidazole (4.04 g, 59.45 mmol) and tert-butyldimethylchlorosilane (4.48 g, 29.72 mmol) were added. The reaction was stirred at room temperature for 24 hours. he mixture was poured in water (70 ml) solution and extracted with diethyl ether (3×70 ml) The organic layers were dried over sodium sulfate and concentrated under reduced pressure. The residue was purified by flash chromatography (Biotage System, column FLASH 40+M™ KP-C18 HS, eluent: gradient acetonitrile/water 65/35 (600 ml), to acetonitrile/water 80/20 during 1200 ml). The product (0.70 g) was obtained.

To a solution of compound J (1.25 g, 4.42 mmol) in dichloromethane (60 ml), 2-(chloroethoxy)-ethoxy ethanol (0.83 g, 5.75 mmol) and DMAP (cat. amount) were added. The reaction was cooled at 0° C. and EDAC (1.10 g, 5.75 mmol) was added. The reaction was stirred at room temperature for 12 hours. The solvent was evaporated under vacuum. The residue was purified by flash chromatography (Biotage System, Cartridge column FLASH 40+M™ KP-Sil, eluent: gradient n-hexane/ethyl acetate 9/1 (40 ml), to n-hexane/ethyl acetate 6/4 during 2000 ml, n-hexane/ethyl acetate 6/4 (400 ml)). The product (1.25 g) was obtained.

L) 2-(2-(2-nitrooxyethoxy)ethoxy)ethyl 4-(tert-butyldimethyl silyloxy)-3-methoxybenzoate

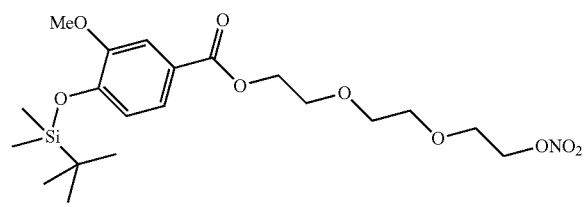

To a solution of compound K (1.53 g, 3.54 mmol) in acetonitrile (45 ml), sodium iodide (3.18 g, 21.24 mmol) was added. The reaction was heated to 120° C. for 20 minutes under microwave irradiation. The resulting mixture was cooled, filtered and the solvent was removed under reduced pressure. To a solution of residue in acetonitrile (45 ml), silver nitrate (2.04 g, 14.16 mmol) was added. The reaction was heated to 120° C. for 5 minutes under microwave irradiation. The resulting mixture was cooled, filtered and the solvent was removed under reduced pressure. The residue was purified by flash chromatography (Biotage System, column FLASH 40+M™ KP-Sil, eluent: gradient n-hexane/ethyl acetate 9/1 (600 ml), to n-hexane/ethyl acetate 6/4 during 2000 ml, n-hexane/ethyl acetate 6/4 (400 ml)). The product (1.37 g) was obtained.

M) 2-(2-(2-nitrooxyethoxy)ethoxy)ethyl 4-hydroxy-3-methoxy benzoate

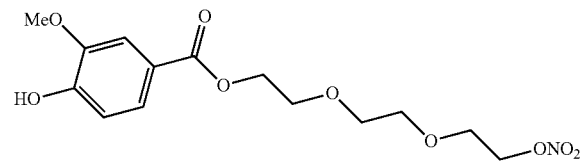

To a solution of compound L (1.10 g, 2.4 mmol) in tetrahydrofurane (40 ml) cooled at −0° C., a solution of tetrabutylamonium floride 1M in tetrahydrofurane (2.4 ml, 2.4 mmol) was added. The reaction was stirred at 0° C. for 20 minutes. The mixture was poured into a 5% aqueous $NaH_2PO_4$ solution (100 ml) and extracted with ethyl acetate (3×50 ml) The organic layers were washed with water (100 ml), dried over sodium sulfate and concentrated under reduced pressure. The residue was purified by flash chromatography (Biotage System, column FLASH 40+M™ KP-Sil, eluent: gradient n-hexane/ethyl acetate 9/1 (600 ml), to n-hexane/ethyl acetate 1/1 during 2000 ml, n-hexane/ethyl acetate 1/1 (400 ml)). The product (0.76 g) was obtained.

N) 2-(2-(2-(nitrooxy)ethoxy)ethoxy)ethyl 4-((2-((6S,9R,10S,11S,13S,16R,17S)-6,9-difluoro-11-hydroxy-16,17-((1-methylethylidene)bis(oxy))-10,13-dimethyl-3-oxo-6,7,8,9,10,11,12,13,14,15,16,17-dodecahydro-3H-cyclopenta [a]phenanthren-17-yl)-2-oxoethoxy)carbonyloxy)-3-methoxy benzoate To a solution of compound H (0.508 g, 0.98 mmol) in dichloromethane (15 ml), diisopropylethylamine (0.18 ml, 1.06 mmol) was added. The reaction was cooled at 0° C. and a solution of compound M (0.37 g, 1.08 mmol) in dichloromethane (3 ml) was added. The reaction was stirred at room temperature for 12 hours. The solvent was evaporated under vacuum. The residue was purified by flash chromatography (Biotage System, column FLASH 40+M™ KP-Sil, eluent: gradient n-hexane/ethyl acetate 8/2 (200 ml), to ethyl acetate 100% during 2400 ml, ethyl acetate 100% (400 ml)). The product (0.70 g) was obtained.

$^1$H-NMR: ($CDCl_3$), δ: 7.70 (2H, d); 7.30 (1H, d); 7.07 (1H, d); 6.45 (1H, s); 6.38 (1H, dd); 5.52-5.32 (1H, m); 5.15-4.91 (2H, dd); 5.04 (1H, d); 4.57-4.49 (4H, m): 4.41 (1H, m); 3.95 (3H, s); 3.84 (2H, dd); 3.78 (2H, dd); 3.68 (4H, m); 2.60-2.10 (4H, m); 1.90-1.47 (10H, m); 1.25 (3H, s); 0.95 (3H, s).

EXAMPLE 4

Compound (6)

Synthesis of 4-(nitrooxy)butyl 3-((2-((6S,9R,10S,11S,13S,16R,17S)-6,9-difluoro-11-hydroxy-16,17-((1-methylethylidene)bis(oxy))-10,13-dimethyl-3-oxo-6,7,8,9,10,11,12,13,14,15,16,17-dodecahydro-3H-cyclopenta[a]phenanthren-17-yl)-2-oxoethoxy)carbonyloxy)-4,5-dihydroxybenzoate

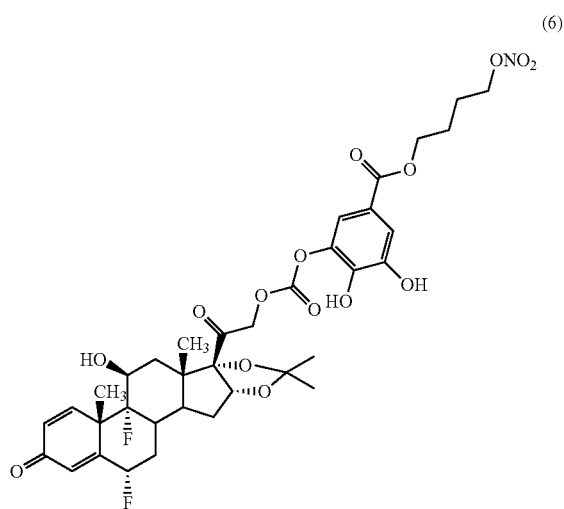

O) Methyl 7-hydroxy-2-(4-methoxyphenyl)benzo[d][1,3]dioxole-5-carboxylate

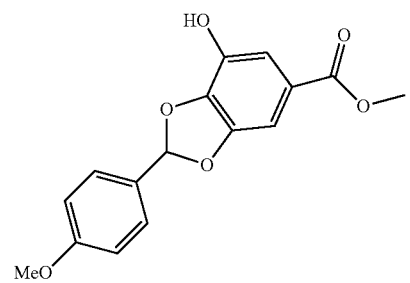 [SMILES: COC(=O)c1cc(O)c2c(c1)OC(c1ccc(OC)cc1)O2]

To a suspension of methyl gallate (10 g, 54.3 mmol) in toluene (25 ml), p-toluensulfonic acid (29 mg) and p-anisaldehyde dimethylacetal (11.56 ml, 67.88 mmol) were added. The reaction was refluxed for 1.5 hours with continuous removal of water. The mixture was diluted with dichloromethane (70 ml) and washed with a saturated aqueous NaHCO$_3$ solution (100 ml) and extracted with ethyl acetate (3×50 ml) The organic layer was washed with water (100 ml), dried over sodium sulphate and concentrated under reduced pressure. The residue was crystallized by n-hexane. The product (8.6 g) was obtained.

P) 7-Hydroxy-2-(4-methoxyphenyl)benzo[d][1,3]dioxole-5-carboxylic acid

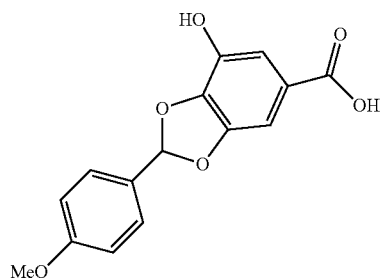 [SMILES: COc1ccc(C2Oc3cc(C(=O)O)cc(O)c3O2)cc1]

To a suspension of compound O (8.6 g, 28.41 mmol) in water/ethanol 5/95 (260 ml), sodium hydroxide (2.5 ml, 62.5 mmol) was added. The reaction was refluxed for 15 hours The solvent was evaporated under vacuum. The residue was dissolved in water (150 ml) and extracted with ethyl acetate (100 ml). The aqueous layer was acidified to pH 4 with 1N aqueous HCl and extracted with ethyl acetate (6×50 ml) The organic layers were dried over sodium sulphate and concentrated under reduced pressure. The crude product (5.78 g) was used in the next step without any purification.

Q) 4-(nitrooxy)butyl-7-hydroxy-2-(4-methoxyphenyl)benzo[d][1,3]dioxole-5-carboxylate

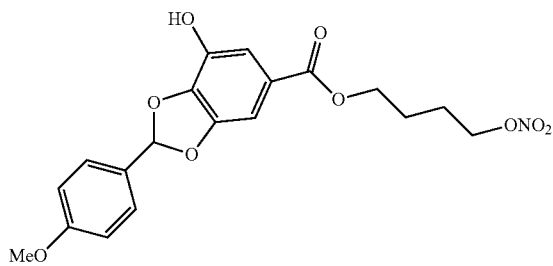

To a solution of compound P (5.78 g, 20.05 mmol) in N,N-dimethylformamide (50 ml), cesium carbonate (6.52 g, 20.05 mmol) was added. The reaction was cooled at 0° C. and a 20% solution of 1-bromo-4-(nitrooxy)butane in dichloromethane (19.85 g) was added. The reaction was stirred at room temperature for 40 hours. The mixture was poured into a 5% aqueous NaH$_2$PO$_4$ solution and extracted with diethyl ether (2×70 ml) The organic layers were washed with water (50 ml), dried over sodium sulphate and concentrated under reduced pressure. The residue was purified by flash chromatography (Biotage System, SNAP Cartridge silica 100 g, eluent: gradient n-hexane/ethyl acetate 9/1 (200 ml), to n-hexane/ethyl acetate 1/1 during 1200 ml, n-hexane/ethyl acetate 1/1 (400 ml)). The product (4.36 g) was obtained.

R) 4-(Nitrooxy)butyl 7-((2-((6S,9R,10S,11S,13S,16R,17S)-6,9-difluoro-11-hydroxy-16,17-((1-methylethylidene)bis(oxy))-10,13-dimethyl-3-oxo-6,7,8,9,10,11,12,13,14,15,16,17-dodecahydro-3H-cyclopenta[a]phenanthren-17-yl)-2-oxoethoxy)carbonyloxy)-2-(4-methoxyphenyl)benzo[d][1,3]dioxole-5-carboxylate

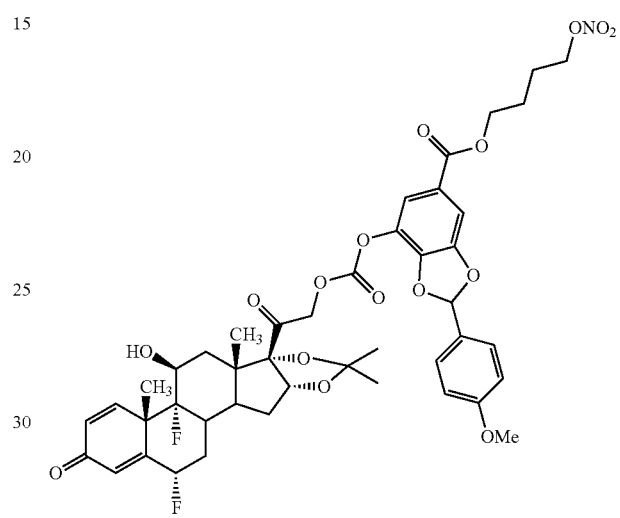

To a solution of compound Q (0.519 g, 1.28 mmol) in dichloromethane (13 ml), diisopropylethylamine (0.179 ml, 1.28 mmol) was added. The reaction was cooled at 0° C. and a solution of compound H (0.6 g, 1.16 mmol) in dichloromethane (3 ml) was added. The reaction was stirred at room temperature for 16 hours. The solvent was evaporated under vacuum. The residue was purified by flash chromatography (Biotage System, SNAP Cartridge silica 100 g, eluent: gradient n-hexane/ethyl acetate 9/1 (200 ml), to n-hexane/ethyl acetate 3/7 during 1200 ml, n-hexane/ethyl acetate 3/7 (400 ml)). The product (0.979 g) was obtained.

4-(Nitrooxy)butyl 3-((2-((6S,9R,10S,11S,13S,16R,17S)-6,9-difluoro-11-hydroxy-16,17-((1-methylethylidene)bis(oxy))-10,13-dimethyl-3-oxo-6,7,8,9,10,11,12,13,14,15,16,17-dodecahydro-3H-cyclopenta[a]phenanthren-17-yl)-2-oxoethoxy)carbonyloxy)-4,5-dihydroxybenzoate To a solution of compound R (0.97 g, 1.09 mmol) in tetrahydrofurane (22.4 ml), 1N aqueous HCl (22.4 ml) was added. The reaction was stirred at room temperature for 17 hours. The solvent was evaporated under vacuum. The residue was extracted with ethyl acetate (2×30 ml) The organic layers were dried over sodium sulphate and concentrated under reduced pressure. The residue was purified by flash chromatography (Biotage System, purified by flash chromatography (Biotage System, SNAP Cartridge silica 100 g, eluent: gradient acetone/dichloromethane 5/95 (200 ml), to acetone/dichloromethane 2/8 during 900 ml, to acetone/dichloromethane 3/7 during 600 ml). The product (0.344 g) was obtained.

$^1$H-NMR: (CDCl$_3$), δ: 7.51 (2H, dd); 7.14 (1H, d); 6.47 (1H, s); 6.40 (1H, dd); 5.52-5.32 (1H, m); 5.24-4.93 (2H, dd); 5.03 (1H, d); 4.53 (2H, t): 4.43-4.33 (3H, m); 2.54-2.17 (4H, m); 2.00-1.65 (8H, m); 1.53 (3H, s); 1.47 (3H,s); 1.25 (3H,s); 0.94 (3H, s).

EXAMPLE 5

Compound (10)

Synthesis of 4-(nitrooxy)butyl 3-((2-((9R,10S,11S, 13S,16R,17S)-9-fluoro-11-hydroxy-16,17-((1-methylethylidene)bis(oxy))-10,13-dimethyl-3-oxo-6,7,8, 9,10,11,12,13,14,15,16,17-dodecahydro-3H-cyclopenta[a]phenanthren-17-yl)-2-oxoethoxy) carbonyloxy)-4,5-dihydroxybenzoate

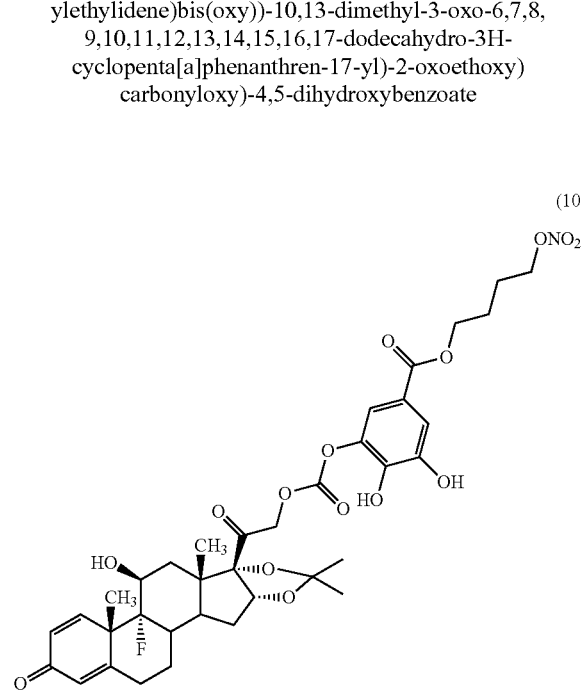

(10)

S) 2-((9R,10S,11S,13S,16R,17S)-9-fluoro-11-hydroxy-16,17-((1-methylethylidene)bis(oxy))-10,13-dimethyl-3-oxo-6,7,8,9,10,11,12,13,14,15,16,17-dodecahydro-3H-cyclopenta[a]phenanthren-17-yl)-2-oxoethyl carbonochloridate

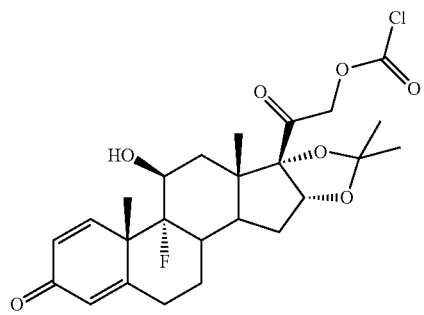

To a solution of triamcinolone acetonide (3 g, 6.9 mmol) in tetrahydrofurane (33 ml), cooled at 0° C. and under N$_2$, a 20% toluene solution of phosgene (21.8 ml, 41.4 mmol) was added. The reaction was stirred at 0° C. for 1 hour and at room temperature for 17 hours. The excess of phosgene was removed by heating at 40° C. for 30 minutes. The solvent was evaporated under vacuum. The crude product was used in the next step without any purification.

T) 4-(Nitrooxy)butyl 7-((2-((9R,10S,11S,13S,16R, 17S)-9-fluoro-1-hydroxy-16,17-((1-methylethylidene)bis(oxy))-10,13-dimethyl-3-oxo-6,7,8,9,10, 11,12,13,14,15,16,17-dodecahydro-3H-cyclopenta[a] phenanthren-17-yl)-2-oxoethoxy)carbonyloxy)-2-(4-methoxyphenyl)benzo[d][1,3]dioxole-5-carboxylate

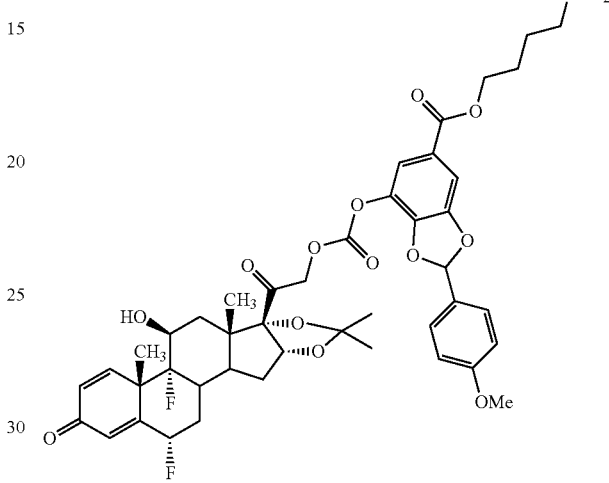

To a solution of compound Q (0.583 g, 1.32 mmol) in dichloromethane (14 ml), diisopropylethylamine (0.231 ml, 1.32 mmol) was added. The reaction was cooled at 0° C. and a solution of compound S (0.6 g, 1.2 mmol) in dichloromethane (3 ml) was added. The reaction was stirred at room temperature for 16 hours. The solvent was evaporated under vacuum. The residue was purified by flash chromatography (Biotage System, SNAP Cartridge silica 100 g, eluent: gradient n-hexane/ethyl acetate 9/1 (200 ml), to n-hexane/ethyl acetate 3/7 during 1200 ml, n-hexane/ethyl acetate 3/7 (400 ml)). The product (0.819 g) was obtained.

U) 4-(Nitrooxy)butyl-9-fluoro-11-hydroxy-16,17-((1-methylethylidene)bis(oxy))-10,13-dimethyl-3-oxo-6,7,8,9,10,11,12,13,14,15,16,17-dodecahydro-3H-cyclopenta[a]phenanthren-17-yl)-2-oxoethoxy) carbonyloxy)-4,5-dihydroxybenzoate To a solution of compound T (0.81 g, 0.93 mmol) in tetrahydrofurane (19.5 ml), 1N aqueous HCl (19.5 ml) was added. The reaction was stirred at room temperature for 18 hours. The solvent was evaporated under vacuum. The residue was extracted with ethyl acetate (2×30 ml) The organic layers were dried over sodium sulfate and concentrated under reduced pressure. The residue was purified by flash chromatography (Biotage System, purified by flash chromatography (Biotage System, SNAP Cartridge silica 100 g, eluent: gradient acetone/dichloromethane 5/95 (200 ml), to acetone/ dichloromethane 3/7 during 900 ml, acetone/dichloromethane 3/7 (200 ml). The product (0.245 g) was obtained.

$^1$H-NMR: (CDCl$_3$), δ: 7.51 (2H, dd); 7.23 (1H, d); 6.38 (1H, s); 6.18 (1H, dd); 5.21-4.90 (2H, dd); 5.03 (1H, d); 4.53 (2H, t): 4.41-4.32 (3H, m); 2.69-2.35 (4H, m); 2.00-1.65 (10H, m); 1.53 (3H, s); 1.45 (3H,s); 1.24 (3H,s); 0.94 (3H, s).

EXAMPLE 6

Compound (17)

2-(2-(2-(nitrooxy)ethoxy)ethoxy)ethyl 4-((2-((9R,10S,11S,13S,16R,17S)-9-fluoro-11-hydroxy-16,17-((1-methyl ethylidene)bis(oxy))-10,13-dimethyl-3-oxo-6,7,8,9,10,11,12,13,14,15,16,17-dodecahydro-3H-cyclopenta[a]phenanthren-17-yl)-2-oxoethoxy)carbonyloxy)-3-methoxybenzoate

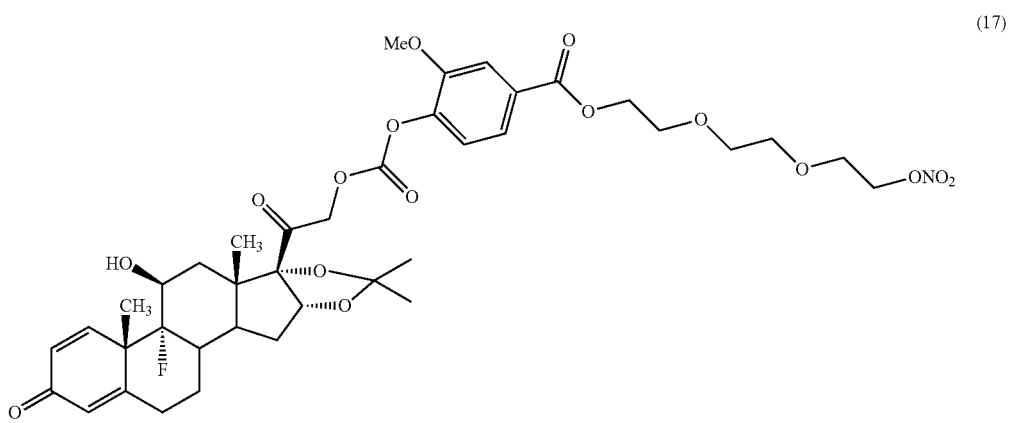

(17)

The compound was synthesized using the procedure described in example 3 starting from compound S and compound M.

$^1$H-NMR: (CDCl$_3$), δ: 7.71 (2H, d); 7.26 (1H, d); 7.15 (1H, d); 6.31 (1H, dd); 6.12 (1H, s); 5.12 (1H, d); 4.91 (1H, d); 5.01 (2H, d); 4.56 (2H, m); 4.49 (2H, t): 4.40 (1H, m); 3.95 (3H, s); 3.79 (2H, t); 3.76 (2H, m); 3.67 (4H, m); 2.65-2.35 (4H, m); 2.15-2.00 (1H, m); 1.92-1.84 (1H, m); 1.72-1.55 (2H, m); 1.51 (3H, s); 1.45 (3H,s); 1.25 (5H, m); 0.93 (3H, s).

EXAMPLE 7

Compound (18)

4-(nitrooxy)butyl 4-((2-((9R,10S,11S,13S,16R,17S)-9-fluoro-11-hydroxy-16,17-(1-methylethylidenebis(oxy))-10,13-dimethyl-3-oxo-6,7,8,9,10,11,12,13,14,15,16,17-dodecahydro-3H-cyclopenta[a]phenanthren-17-yl)-2-oxoethoxy)carbonyloxy)-3-methoxybenzoate

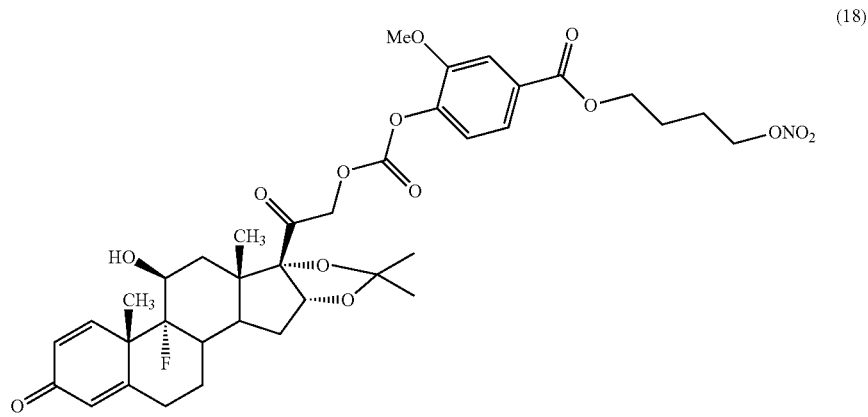

(18)

The compound was synthesized using the procedure described in example 1 starting from triamcinolone acetonide and compound B.

$^1$H-NMR: (CDCl$_3$), δ: 7.65 (2H, m); 7.26 (1H, d); 7.17 (1H, d); 6.40 (1H, dd); 6.10 (1H, s); 5.11-4.84 (2H, dd); 4.99 (1H, d); 4.53 (2H, t); 4.37 (2H, t); 3.93 (3H, s); 2.71-2.30 (5H, m); 2.00-1.50 (6H, m); 1.87 (4H, m); 1.50 (3H, s); 1.41 (3H, s); 1.22 (3H, s); 0.92 (3H, s).

EXAMPLE F1

Assay on Vascular Tone

Test Compounds:
- Compound (1) described in Ex. 1
- Compound (3) described in Ex. 2
- Compound (5) described in Ex. 3
- Compound (6) described in Ex. 4
- Compound (10) described in Ex. 5
- Compound (18) described in Ex. 7

Reference Compounds
Fluocinolone acetonide (FC)
Triamcinolone acetonide (TAAC)

The ability of the compounds of the invention to induce vasorelaxation in comparison to precursor compounds was tested in vitro in isolated rabbit thoracic aorta preparations (Wanstall J. C. et al., Br. J. Pharmacol., 134:463-472, 2001). Male New Zealand rabbits (1,8-2 Kg) were used. The animals were anaesthetized with sodium thiopental (50 mg/kg, iv), sacrificed by exsanguinations and then the thorax was opened and the aorta dissected. The aortas were placed immediately in Krebs-HEPES buffer (pH 7.4; composition mM: NaCl 130.0, Kcl 3.7, NaHCO$_2$ 14.9, KH$_2$PO$_4$ 1.2, MgSO$_4$.7H$_2$O 1.2, Glucose 11.0, HEPES 10.0, CaCl$_2$.2H$_2$O 1.6) and cut into ring segments (4-5 mm in length). Each ring was placed in a 5 ml tissue bath filled with Krebs-HEPES buffer (37° C.) aerated with 95% O$_2$ and 5% CO$_2$ and was then attached to a force transducer (Grass FT03), connected to a BIOPAC MP150 System for measurement of the isometric tension[2]. The preparations were allowed to equilibrate for 1 h at a resting tension of 2 g with changes of the buffer every 15 minutes and then stimulated by exposure to 90 mM KCl (3 times) with intervening washings. After equilibration, the rings were precontracted submaximally with methoxamine (3 μM) and, when the contraction reach a steady state a cumulative concentration-response curve to the test compounds was obtained. The time intervals between doses were based on the time needed to reach a full a steady state response.

Responses to test compounds were expressed as a percentage of residual contraction and plotted against concentration of test compound. EC$_{50}$ values (where EC$_{50}$ is the concentration producing 50% of the maximum relaxation to the test compound) were interpolated from these plots.

As shown in Table 1, the test compounds were able to induce relaxation in a concentration-dependent manner.

TABLE 1

| Assay on vascular tone | |
| --- | --- |
| Test Compound | EC$_{50}$ (μM) |
| FC | no effect |
| Compound (1) | 2.2 |
| Compound (3) | 0.21 ± 0.07 |
| Compound (5) | 0.83 ± 0.25 |
| Compound (6) | 1.44 ± 0.41 |
| TAAC | no effect |
| Compound (18) | 1.56 |
| Compound (10) | 2.35 ± 0.98 |

EXAMPLE F2

Evaluation of the efficacy of the compounds of the invention in an in vivo VEGF-induced leakage rat model.

Vascular endothelial growth factor (VEGF) activates common pathways of vascular leakage associated with various pathological processes including diabetic macular edema (DME) Test Compounds:
- Compound (1) disclosed in Example 1
- Fluocinolone acetonide (FC): reference compound of compound (1)
- Compound (18) described in Example 7
- Triamcinolone acetonide (TAAC): reference compound of compound (18)

Male Sprague Dawley rats (~250 g; Charles River laboratory) were anesthetized with isoflurane inhalation and a drop of 0.5% tetracaine was topically applied on the eyes. Pupils were dilated with 1% topical cyclopentolate hydrochloride to see the needle to guide the intravitreal injection. Recombinant rat vascular endothelial growth factor (VEGF; 100 ng/eye) or VEGF at 100 ng/eye plus test compounds were prepared in 0.5% carboxymethyl cellulose (CMC) in sterile saline and was injected into the vitreous with a 30-gauge needle (Xu, Q., et al. Invest. Ophthalmol. Vis. Sci., 42:789-794, 2001). The compounds of the invention were compared to corresponding steroid cores at equimolar doses. For example, to compare to fluocinolone acetonide at both 25 and 50 μg/eye, compound (1) was dosed at 42.4 and 84.7 μg/eye, respectively. Control animals received vehicle. Compound (18) was similarly dosed alongside triamcinolone acetonide for comparison.

Retinal vascular leakage was measured as described previously (Xu, Q., et al. Invest. Ophthalmol. Vis. Sci., 42:789-794, 2001). After about 18 hours post injection of test compounds, rats were anesthetized with ketamine (80 mg/kg) and xylazine (4 mg/kg) IP. Then 45 mg/kg Evans blue (EB) was injected into the jugular vein. The dye was allowed to circulate for 2 hours. The chest cavity was opened and rats then perfused with 1% formalin in 0.5 M citrate buffer (pH 3.5, 37° C.) through the left ventricle. Retinas were carefully dissected from enucleated eyes, placed in pre-weighed Eppendorf tubes, dried in speed vacuum overnight and dry weights recorded. Evans blue was extracted by incubating each retina in 120 μl formamide for 18 hours at 70° C., centrifuged for 2 hours at 6000 rpm. Absorbance of 60 μl of extract was measured at 620 nm and background absorbance was determined at 740 nm. Net absorbance was calculated by subtracting the background 740 nm from that at 620 nm. Measurement of a standard curve of Evans blue in formamide was also done and Evans blue leakage expressed as μl/g/h was calculated as shown below:

[EB(ng/ml)×120 (μl)×1000]/[dry weight retina (mg)× circulation time (h)×plasma EB(ng/ml)×100]

Figure 1B:
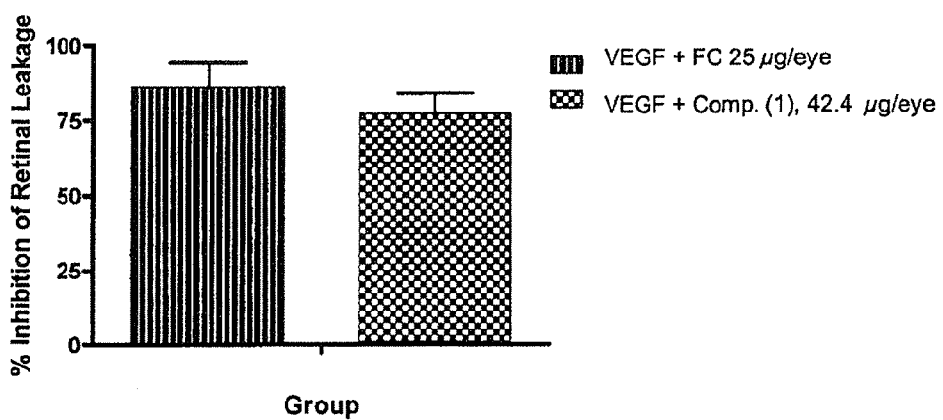
Figure 2A:
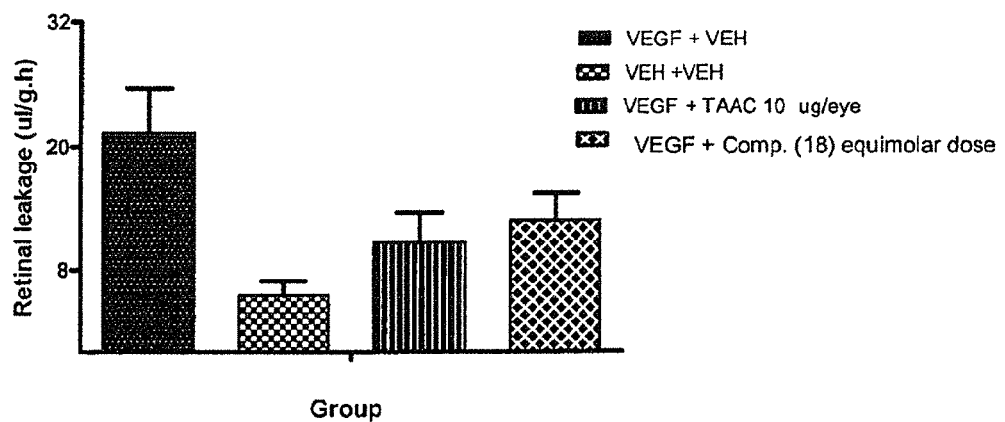
Figure 2B:
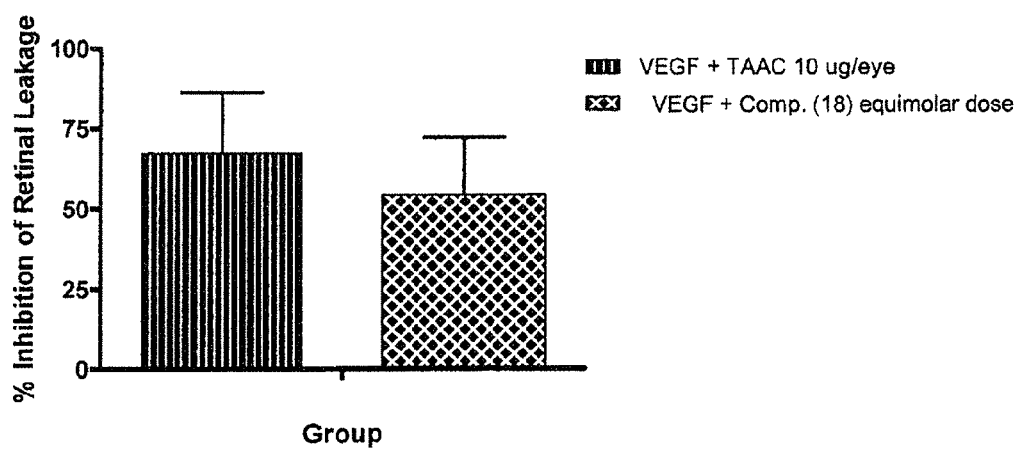

As shown in FIG. 1a below, intravitreal injection of 100 ng VEGF resulted in a 3.5-fold increase (n=17, P<0.05) in vascular permeability 18 hours after injection. Treatment with 25 μg/eye of fluocinolone acetonide and 42.4 μg/eye of compound (1) inhibited the VEGF-induced leakage by 86.1% and 77.1%, respectively (FIGS. 1a and 1b, n=9, P<0.05). Similarly a 10 μg/eye dose of triamcinolone acetonide and its equivalent dose of compound (18) caused reduction by 67.5% and 54.3%, respectively (FIGS. 2a and 2b). In all cases, the inhibition of leakage was similar in magnitude for both compounds of the invention (compounds (1) and (18)) and its corresponding steroid core.

EXAMPLE F3

Evaluation of the amelioration of steroid-induced intraocular pressure (IOP) elevation in vivo in rats by the compound of the invention.

Test Compounds:

Compound (1) disclosed in Example 1

Fluocinolone acetonide (FC): reference compound

Des-nitro analog of compound (1): Butyl 4-((2-((6S,9R,10S,11S,13S,16R,17S)-6,9-difluoro-11-hydroxy-16,17-16,17-(1-methylethylidenebis(oxy))-10,13-dimethyl-3-oxo-6,7,8,9,10,11,12,13,14,15,16,17-dodecahydro-3H-cyclopenta[a]phenanthren-17-yl)-2-oxoethoxy)carbonyloxy)-3-methoxybenzoate.

Male Brown Norway rats (250-275 g; Charles River laboratory) were acclimated for a week before IOP measurements. Baseline IOP measurements with Tonolab Tonometer (Tiolat Inc) were done in conscious rats (Pease, M. E., et al *J. Glaucoma*, 15:512-519, 2006) before intravitreal injection of test compounds. Then the rats were anesthetized with isoflurane inhalation and a drop of 0.5% tetracaine was topically applied on the eyes. Pupils were dilated with 1% topical cyclopentolate hydrochloride and 2.5% phenylephrine HCl to see the needle to aim the intravitreal injection of test compounds. The compound (I) was compared to corresponding steroid core and to the des-nitro analog at equimolar doses. For example, to compare to fluocinolone acetonide at both 25 and 50 μg/eye, compound (1) was dosed at 42.4 and 84.7 μg/eye, respectively. The des-nitro analog of compound (1) was dosed at 39.1 μg/eye (equivalent for 25 μg FC). Control animals received vehicle.

Five measurements were averaged for each time point. IOP measurements were taken at one and two weeks after intravitreal injection of test compounds.

Figure 3:
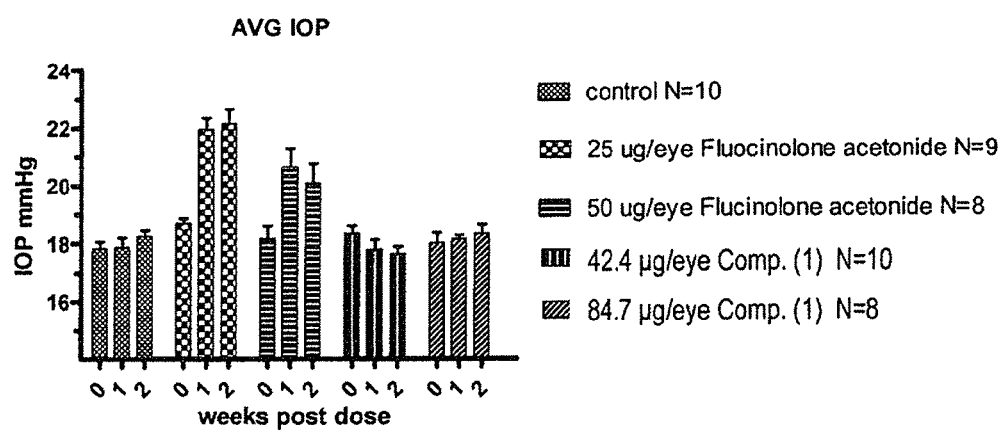
Figure 4:
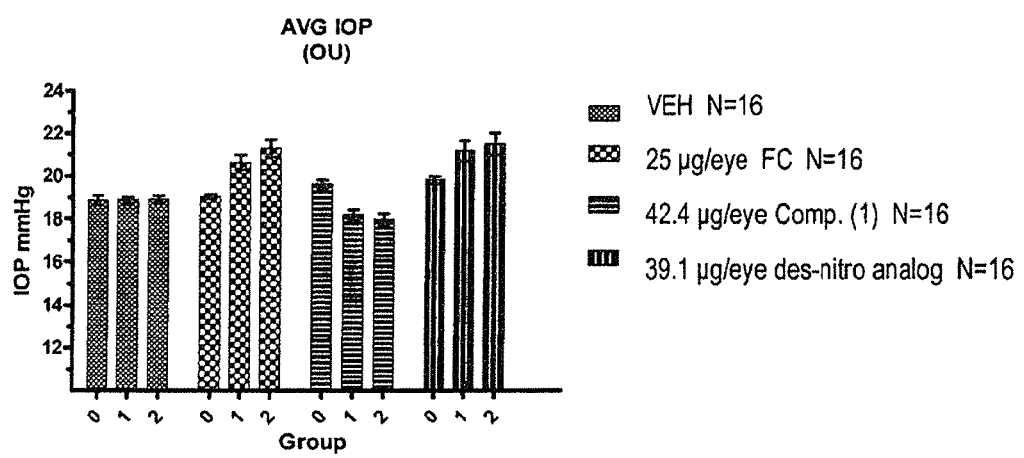

Baseline IOP in the Brown Norway rats was 18 mm Hg. As shown in FIG. 3 below, one week after injection of fluocinolone acetonide, IOP increased by 4 mm Hg with 25 μg/eye and 3 mm Hg with 50 μg/eye, respectively. This was maintained after two weeks (p<0.05). However, injection of compound (1) at 25 or 50 μg/eye equivalent (42.4 and 84.7 μg/eye, respectively) caused no change in IOP at one or two week time points (FIG. 3). In another experiment seen in FIG. 4 below, des-nitro analog of compound (1) at 25 μg/eye equivalent (39.1 μg/eye) and fluocinolone acetonide (FC) at 25 μg/eye caused increase in IOP compared to compound (1) at 25 μg/eye equivalent (42.4 μg/eye).

EXAMPLE F4

Evaluation of the efficacy of the compounds on intraocular pressure, ocular haemodynamics and on retina protection and evaluation of inflammatory cytokines content in aqueous humor in an in vivo endothelin-1 (ET-1) induced ischemia in New Zealand White rabbits.

Test Compounds

Compound (1) of Example 1

Fluocinolone acetonide (FC): reference compound

Test System and Methods

Twenty adult male New Zealand Albino rabbits weighing 2-2.5 Kg were used for the experiments. The animals were divided in two groups for the specific treatment chosen. The experimental procedures were conform to those of the Association for Research in Vision and Ophthalmology Resolution on the use of animals and in agreement with the Good Laboratory Practice for the use of animals and were conducted upon authorization of Italian regulation on protection of animals used for experimental and other scientific purpose (DM 116/1992) as well as with the European Union Regulations (OJ of ECL 358/1, Dec. 12, 1986). The rabbits were kept in individual cages, food and water was provided ad libitum. The animals were maintained on a 12-12 h light/dark cycle in a temperature controlled room (22°-23° C.).

Ischemia model of optic injury was obtained throughout by injection, twice a week, for 6 weeks, of endothelin-1 (ET-1) 250 nM, 500 μl of sterile saline, into the posterior vitreous body of both eyes, using a lachrymal cannula, under general anesthesia produced by tiletamine plus zolazepam (Zoletil 100, 0.05 mg/kg) plus xilazine (Xilor 2%, 0.05 ml/kg) i.m.

Fluocinolone acetonide (FC) (0.5 mg/eye in 100 μl of vehicle) or Compound (1) (0.5 mg equivalent/eye in 100 μl of vehicle) were instilled intravitreally (IVT) two weeks after the start of ET-1 treatment (T2), in one eyes, the same volume of vehicle was instilled in the other eye.

Intraocular Pressure

Intraocular pressure (TOP) was measured twice a using a Tono-Pen XL (Medtronic Solan. USA) as described by Maren's group (Exp. Eye Res. (1992) 55: 73-79; Exp. Eye Res. (1993) 57: 67-78) with a two-point standard pressure measurement. Two independent investigators (C.U. and R.M.), using the same tonometer performed IOP measurement.

The data reported in Table 2 show that ET-1 treatment did not modify the IOP in New Zealand White rabbits. Fluocinolone acetonide increased intraocular pressure following ET-1 induced ischemia, on the contrary intraocular pressure following ET-1 induced ischemia was not modified with Compound (1).

TABLE 2

Effect of Fluocinolone acetonide (FC) or compound (1) vs vehicle on IOP.
IOP was taken before daily drug treatment

| | IOP (mmHG) | | | |
|---|---|---|---|---|
| | Vehicle | FC* | Vehicle | Compound (1) |
| basal | 13.00 ± 2.83 | 13.50 ± 0.17 | 12.60 ± 2.01 | 12.70 ± 1.89 |
| ET-1 | 13.50 ± 0.71 | 13.00 ± 2.83 | 12.80 ± 1.55 | 13.30 ± 1.49 |
| I week | 14.00 ± 2.83 | 15.50 ± 0.71 | 13.30 ± 1.49 | 15.30 ± 0.95 |
| II week | 14.40 ± 0.71 | 19.00 ± 0.00 | 13.60 ± 1.96 | 15.00 ± 1.33 |
| III week | 15.00 ± 1.41 | 19.00 ± 1.41 | 13.40 ± 1.51 | 13.50 ± 1.08 |
| IV week | 13.50 ± 1.27 | 20.80 ± 0.71 | 14.20 ± 2.15 | 13.20 ± 1.23 |
| V week | 13.30 ± 1.77 | 22.20 ± 0.00 | 14.10 ± 2.64 | 15.00 ± 2.45 |
| VI week | 13.00 ± 1.56 | 21.10 ± 0.00 | 14.80 ± 2.90 | 15.22 ± 1.09 |

*p < 0,001 vs vehicle (N = 10).

Electroretinogram (ERG)

The Electroretinogram (ERG) was performed in basal condition (T0), before the start of drug treatment (T2) and at the end of drug treatment (T6). Slit lamp and indirect funduscopic examinations were performed on all eyes before the study began. Animals demonstrating corneal or lens opacity or retinal damage before the study were excluded. Topical anaesthesia was applied using one drop 0.2% oxybuprocaine hydrochloride (Novesine, Sandoz). The eyes were dilated by topical application of tropicamide (1%), adapted to darkness for at least 2 hours, and standard ERGs recorded in both eyes using corneal electrodes. The reference and ground electrodes were made of stainless steel surgical needles, and were inserted into the ears. The ERG signals were recorded using Retimax (CSO, Florence, Italy). The dark-adapted scotopic response (rod response) and scotopic flash response (photopic erg cone), were recorded. Flashes varied in intensity from −2.50 to +0.4 log scot cd s/m$^2$. An average of three separate ERGs was determined for each eye. The amplitude (uV) of a- and b-waves were calculated for each step. The baseline values were compared to the response obtained at T2 and at the end of treatment (T6).

ET-1 treatment significantly reduced the amplitude of photopic erg cone (T2, $p<0.05$ versus T0 and T6 $p<0.05$ versus T0).

Results reported in Table 3 show that eyes treated with Fluocinolone acetonide (FC) or Compound (1) exhibited significantly ($p<0.05$ versus vehicle) less reduction in the ERG wave amplitude than those treated with vehicle. Moreover, Compound (1) was slightly more effective than Fluocinolone acetonide.

TABLE 3

Effect of compound (1) or fluocinolone acetonide (FC) vs vehicle on photopic erg cone after ET-1 treatment.

| Photopic erg cone (amplitude (μV)) | | | |
| --- | --- | --- | --- |
| Basal | Vehicle | FC | Compound (1) |
| 147.41 ± 7.43 | 68.85 ± 6.41 | 136.34 ± 11.98 | 140.94 ± 6.22 |

*$p < 0,001$ vs vehicle (N = 8).

Ocular Haemodynamics

Haemodynamic evaluations were performed using an eco-color-doppler DynaView TM II SSD-1700 (Aloka Holding Europe AG, Milan, Italy). All animals underwent Color Doppler Imaging (CDI) investigation before ET-1 injection (T0), before the start of drug instillation (T2) and at the end of the drug treatment (T6). Special attention was devoted to the evaluation of ophthalmic and ciliary artery circulation. Blood flow velocities were measured for each vessel and the Pourcelot Resistance Index (RI) was calculated (Galassi F. et al., Acta Opht. Scand Suppl. (2000) 37-38).

Data reported in table 4 show that Fluocinolone acetonide significantly increased ($p<0.001$ versus vehicle) the resistance index in opthalmic artery indicating a decrease in blood perfusion; this effect was not evident with compound (1) treatment.

TABLE 4

Effect of Compound (1) or Fluocinolone acetonide (FC) vs vehicle on ocular haemodinamic evaluated as resistance index

| | Resistence Index | | |
| --- | --- | --- | --- |
| | Basal | After 2 weeks | After 6 weeks |
| Vehicle | 0.46 ± 0.07 | 0.44 ± 0.06 | 0.48 ± 0.05 |
| FC | 0.45 ± 0.06 | 0.45 ± 0.06 | 0.60 ± 0.04 |
| Compound (1) | 0.43 ± 0.06 | 0.43 ± 0.08 | 0.41 ± 0.03 |

*$p < 0,001$ vs vehicle (N = 10).

Inflammatory Cytokines in Aqueous Humor

Aqueous humor samples were withdrawn from both anterior and posterior chamber fluids of each eye before ET-1 administration (T0), before the administration of Compound (1) or fluorocinolone acetonide (T2), and at the end of treatments (T6). The same volume of saline were reintroduced every time. The aqueous humor samples were immediately frozen at −80° C. until use.

Tumor necrosis factor (TNFα) and interleukin 6 (IL-6) were determined in aqueous humor with a commercial kit using an ELISA method (Amersham Pharmacia Biotech). The minimum detectable concentrations were 0.10 pg/ml for IL-6 and TNFα. The interassay coefficient of variation was 0.7% for all assays. Data reported in table 5 show that ET-1 treatment significantly increased TNFα, IL-6 and VEGF content in aqueous humor samples and that Compound (1) counteracted these effects more efficaciously than fluocinolone acetonide (FC).

TABLE 5

Effects Compound (1) and fluocinolone acetonide (FC) on TNFα, IL-6 and VEGF content in aqueous humor.

| | TNFα (pg/ml) | VEGF (pg/ml) | IL6 (pg/ml) |
| --- | --- | --- | --- |
| Basal | 0.55 ± 0.44 | — | 0.67 ± 0.43 |
| Vehicle | 27.00 ± 4.30 | 166.76 ± 4.54 | 20.47 ± 2.97 |
| FC | 20.76 ± 1.74 | 114.58 ± 5.61 | 16.82 ± 0.98 |
| Compound (1) | 18.93 ± 0.98 | 105.79 ± 1.98 | 15.70 ± 1.73 |

*$p < 0,001$ vs vehicle (N = 6).

Retina Protection: Morphological Analysis

The eyes of each animal was enucleated, cornea and crystalline were removed and the eyes was paraformaldehyde-fixed. Then samples were dehydrated with increasing alcohol concentration (50°-75°-95°-100°). After 95° alcohol treatment, the eyes were divided into two parts following a longitudinal plain from cornea to insertion of optical nerve. Thus the samples were paraffin-embedded. Section 8 μm thick were stained with Haematoxylin-Eosin. Microscopical fields were registered by digitizing camera applied a light microscope with a 20× and 40× objective. On the digitized images was performed a morphological analysis of retinal tissue.

The analysis of retinal tissues showed that long term ET-1 treatment induced profound morphological changes thereby confirming the functional impairment observed in ERG measurements. These morphological changes were not equally present in animals treated with Compound (1), whereas Fluocinolone acetonide was not effective.

Detailed Description of Drawings

FIG. 1$a$: Measured retinal leakage in VEGF-induced rats: control, treated with compound (1) and its corresponding steroid core, fluocinolone acetonide (FC)

FIG. 1b: Resultant percent inhibition of leakage by FC and compound (1), derived from FIG. 1a FIG. 2a: Measured retinal leakage in VEGF-induced rats: control, treated with compound (18) and its corresponding steroid core, triamcinolone acetonide (TAAC)

FIG. 2b: Resultant percent inhibition of leakage by compound (18) and its corresponding steroid core, triamcinolone acetonide (TAAC), derived from FIG. 2a FIG. 3: In vivo IOP effects of intravitreally administered fluocinolone acetonide versus compound (1) in Brown Norway rats FIG. 4: in vivo IOP effects of intravitreally administered fluocinolone acetonide (FC), compound (1), and des-nitro analog of compound (1) in Brown Norway rats

The invention claimed is:

1. A method for treating ocular diseases selected from the group consisting of diabetic macular edema, diabetic retinopathy, macular degeneration, and age-related macular degeneration, comprising administering a compound of the following formula (1):

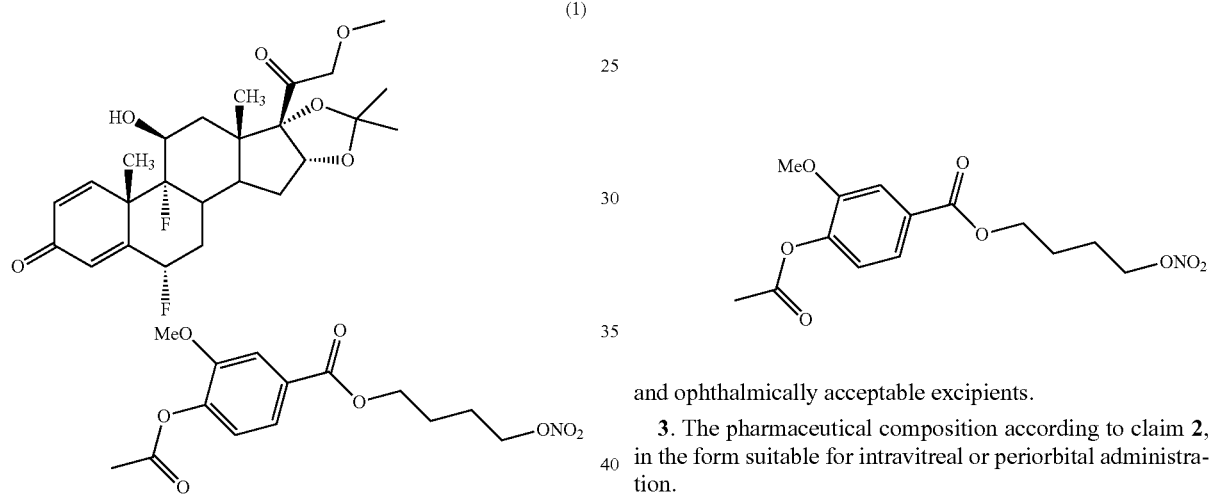

(1)

to a subject in need thereof.

2. A pharmaceutical composition comprising a pharmaceutically effective amount of a compound of the following formula (1):

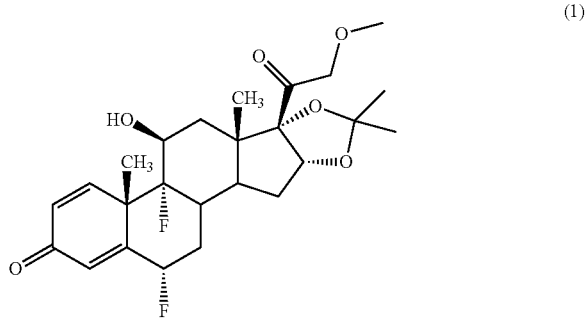

(1)

and ophthalmically acceptable excipients.

3. The pharmaceutical composition according to claim 2, in the form suitable for intravitreal or periorbital administration.

* * * * *